US011512276B2

(12) United States Patent
Smith et al.

(10) Patent No.: US 11,512,276 B2
(45) Date of Patent: *Nov. 29, 2022

(54) METHODS FOR CONTROLLING OXYGEN CONCENTRATION DURING AEROBIC BIOSYNTHESIS

(71) Applicant: INV NYLON CHEMICALS AMERICAS, LLC, Wilmington, DE (US)

(72) Inventors: Gary J. Smith, North Yorkshire (GB); Paul S. Pearlman, Thornton, PA (US); Gregory S. Kirby, Avondale, PA (US)

(73) Assignee: INV NYLON CHEMICALS AMERICAS, LLC, Wilmington, DE (US)

( * ) Notice: Subject to any disclaimer, the term of this patent is extended or adjusted under 35 U.S.C. 154(b) by 204 days.

This patent is subject to a terminal disclaimer.

(21) Appl. No.: 16/372,099

(22) Filed: Apr. 1, 2019

(65) Prior Publication Data

US 2019/0300839 A1    Oct. 3, 2019

Related U.S. Application Data

(60) Provisional application No. 62/650,585, filed on Mar. 30, 2018.

(51) Int. Cl.
*C12P 1/00* (2006.01)
*C12P 5/00* (2006.01)
*C12M 1/34* (2006.01)

(52) U.S. Cl.
CPC .............. *C12M 41/34* (2013.01); *C12P 1/00* (2013.01); *C12P 5/00* (2013.01)

(58) Field of Classification Search
CPC .............. C12P 1/00; C12P 5/00; C12M 41/34
See application file for complete search history.

(56) References Cited

U.S. PATENT DOCUMENTS

| | | | |
|---|---|---|---|
| 3,957,876 A | 5/1976 | Rapoport et al. | |
| 4,554,101 A | 11/1985 | Hopp | |
| 6,207,217 B1 | 3/2001 | Peoples et al. | |
| 6,888,034 B1 | 5/2005 | Landray et al. | |
| 7,384,783 B2 | 6/2008 | Kunas et al. | |
| 8,603,518 B2 | 12/2013 | Boon et al. | |
| 8,809,027 B1 | 8/2014 | Lynch et al. | |
| 8,986,960 B2 | 3/2015 | Sichwart | |
| 9,221,737 B2 | 12/2015 | Valdez | |
| 9,580,733 B2 | 2/2017 | Botes et al. | |
| 9,637,764 B2 | 5/2017 | Botes et al. | |
| 9,650,653 B2 | 5/2017 | Pearlman et al. | |
| 9,862,973 B2 | 1/2018 | Botes et al. | |
| 9,920,339 B2 | 3/2018 | Kadi et al. | |
| 10,072,150 B2 | 9/2018 | Conradie et al. | |
| 10,196,657 B2 | 2/2019 | Pearlman et al. | |
| 10,577,634 B2 | 3/2020 | Pearlman et al. | |
| 10,975,363 B2 | 4/2021 | Foster et al. | |
| 2007/0264688 A1 | 11/2007 | Venter et al. | |
| 2007/0269862 A1 | 11/2007 | Glass et al. | |
| 2011/0125118 A1* | 5/2011 | Lynch ........................... | 604/367 |
| 2012/0003706 A1 | 1/2012 | Hickey | |
| 2012/0064622 A1 | 3/2012 | Fischer et al. | |
| 2013/0034884 A1 | 2/2013 | Burgard et al. | |
| 2013/0065285 A1 | 3/2013 | Sefton | |
| 2013/0189763 A1 | 7/2013 | Dalla-betta et al. | |
| 2013/0323714 A1 | 12/2013 | Cheng et al. | |
| 2014/0248687 A1* | 11/2014 | Kelly et al. ............ | C12N 15/74 435/252.3 |
| 2015/0132815 A1 | 5/2015 | Hickey | |
| 2015/0315599 A1 | 11/2015 | Shetty et al. | |
| 2016/0176813 A1 | 6/2016 | Valdez | |
| 2017/0218406 A1 | 8/2017 | Conradie et al. | |
| 2018/0023103 A1 | 1/2018 | Foster et al. | |
| 2018/0023104 A1 | 1/2018 | Cartman et al. | |
| 2018/0100160 A1 | 4/2018 | Bawdon et al. | |

(Continued)

FOREIGN PATENT DOCUMENTS

| | | |
|---|---|---|
| EP | 0995490 | 4/2000 |
| EP | 1728853 A1 | 12/2006 |

(Continued)

OTHER PUBLICATIONS

NETL brochure, "Syngas composition", accessed online on (www.netl.doe.gov/research/coal/energy systems/gasification/gasifipedia/syngas-composition), Jul. 3, 2021, total pp. 1-2. (Year: 2021).*
International Application No. PCT/US2019/025194, "Invitation to Pay Additional Fees and, Where Applicable, Protest Fee", dated Jul. 1, 2019, 15 pages.
Tanaka et al., "Production of Poly(D-3-Hydroxybutyrate) from CO2, H2, and O2 by High Cell Density Autotrophic Cultivation of Alcaligenes Eutrophus", Biotechnology and Bioengineering, vol. 45, No. 3, Feb. 5, 1995, pp. 268-275.
Abayomi, Oluwanbe Johnson , et al., "An engineered constitutive promoter set with broad activity range for Cupriavidus necator H16", Acs Synthetic Biology, vol. 7, (Jun. 27, 2018), XP002792846, Jun. 27, 2018, pp. 1918-1928.

(Continued)

*Primary Examiner* — Satyendra K Singh

(57) ABSTRACT

The present disclosure provides methods for controlling oxygen concentration during aerobic biosynthesis, e.g., fermentation. The method may comprise feeding an oxygen-containing gas into a vessel including a fermentation feedstock and reacting the fermentation feedstock with the oxygen-containing gas to form a broth including a gaseous phase dispersed within the broth. The gaseous phase may comprise any unreacted oxygen from the oxygen-containing gas. The method further includes reducing the concentration of the unreacted oxygen in the dispersed gaseous phase to less than the limiting oxygen concentration ("LOC") for flammability before separating the gaseous phase from the fermentation broth. The concentration of the unreacted oxygen in the gaseous phase is reduced by employing oxygen removal schemes or oxygen dilution schemes.

18 Claims, 4 Drawing Sheets

(56) References Cited

U.S. PATENT DOCUMENTS

| | | | |
|---|---|---|---|
| 2018/0327705 A1* | 11/2018 | Matsuka | C12M 27/04 |
| 2019/0124947 A1 | 5/2019 | Peariman et al. | |
| 2019/0300839 A1 | 10/2019 | Smith et al. | |
| 2019/0316072 A1 | 10/2019 | Smith et al. | |
| 2019/0338320 A1 | 11/2019 | Foster et al. | |
| 2019/0352674 A1 | 11/2019 | Foster et al. | |
| 2019/0352682 A1 | 11/2019 | Foster et al. | |
| 2019/0359957 A1 | 11/2019 | Foster et al. | |

FOREIGN PATENT DOCUMENTS

| | | |
|---|---|---|
| EP | 1938892 A1 | 7/2008 |
| EP | 3399015 | 11/2018 |
| JP | S49124358 A | 11/1974 |
| JP | 2009225662 A | 10/2009 |
| JP | 2013179909 A | 9/2013 |
| WO | 2008094282 A1 | 8/2008 |
| WO | 2010003007 | 1/2010 |
| WO | 2010069313 | 6/2010 |
| WO | 2013090769 A2 | 6/2013 |
| WO | 2013186340 A1 | 12/2013 |
| WO | 2014093505 A1 | 6/2014 |
| WO | 2014105793 A1 | 7/2014 |
| WO | 2014105797 A2 | 7/2014 |
| WO | 2015117019 A1 | 8/2015 |
| WO | 2015149147 A1 | 10/2015 |
| WO | 2015195654 A1 | 12/2015 |
| WO | 2017115855 | 7/2017 |
| WO | 2017165244 A1 | 9/2017 |
| WO | 2018005//0 A2 | 1/2018 |
| WO | 2018022595 A1 | 2/2018 |
| WO | 2018022633 A1 | 2/2018 |
| WO | 2018106549 A1 | 6/2018 |
| WO | 2013152051 A2 | 10/2019 |
| WO | 2019191761 A1 | 10/2019 |
| WO | 2019191763 A1 | 10/2019 |
| WO | 2019191767 A1 | 10/2019 |
| WO | 2019191770 A1 | 10/2019 |
| WO | 2019191772 A1 | 10/2019 |
| WO | 2019213108 A1 | 11/2019 |
| WO | 2019213118 A1 | 11/2019 |

OTHER PUBLICATIONS

Atlic, et al., "Continuous Production of Poly([R]-3-Hydroxybutyrate) by Cupriavidus necator in a Multistage Bioreactor Cascade", Applied Microbialogy and Biotechnology, vol. 91, 2011, pp. 295-304.

Byrd, et al. "Bacterial Control of Agromyces Ramosus in Soil Canadian Journal of Microbiology", vol. 31, No. 12, 1985, pp. 1157-1163.

Chae, Tong Un., et al., "Metabolic engineering of Escherichia colifor the production of four-, five- and six-carbon lactams Metabolic Engineering", Academic Press, Us, vol. 41, Apr. 5, 2017, pp. 82-91.

Chi, Nguyen, et al., "Trapping the dynamic acyl carrier protein in fatty acid biosynthesis", Nature, vol. 505, No. 7483, Dec. 22, 2013, pp. 427-431.

Eggers, et al., "Impact of Ralstonia eutropha's Poly(3-Hydroxybutyrate) (PHB) Depolymerases and Phasins on PHB Storage in Recombinant Escherichia coli", Applied and Environmental Microbiology, vol. 80, No. 24, Dec. 2014, pp. 7702-7709.

Feng, Yanbin, et al., "Tuning of acyl-ACP thioesterase activity directed for tailored fatty acid synthesis Applied Microbiology and Biotechnology", Springer, De, vol. 102, No. 7, Feb. 22, 2018, pp. 3173-3182.

Fernando, Silva, et al., "Impact of nitrogen feeding regulation on polyhydroxyalkanoates production by mixed microbial cultures", New Biotechnology, vol. 37, XP029943712 2017, pp. 90-98.

Gabriela, Montiel-Jarillo, et al., "Enrichment of a mixed microbial culture for polyhydroxyalkanoates production: Effect of pH and N and P concentrations", Science of the Total Environment, vol. 583, XP029914697, 2017, pp. 300-307.

Girdhar, Amandeep, et al., "Process Parameters for Influencing Polyhydroxyalkanoate Producing Bacterial Factories: An Overview", Journal of Petroleum & Environmental Biotechnology, vol. 4, No. 5, 2013, pp. 8.

Hanko, Erik K. R.., et al., "Characterisation of a 3-hydroxypropionic acid-inducible system from Pseudomonas putida for orthogonal gene expression control in Escherichia coli and Cupriavidus necator", Scientific Reports, vol. 7, XP002792878, 2017, pp. 1-12.

Horvat, et al., "Mathematical Modelling and Process Optimization of a Continuous 5-Stage Bioreactor Cascade for Production of Poly[-(R)-3-Hydroxybutyrate] by Cupriavidus Necator", Bioprocess Biosyst Eng, vol. 36, 2013, pp. 1235-1250.

Hun-Suk, Song, et al. "Enhanced isobutanol production from acetate by combinatorial overexpression of acetyl-CoA synthetase and anaplerotic enzymes in engineered Escherichia coli", Biotechnology and Bioengineering, vol. 115, (May 2, 2018), XP002792879, May 2, 2018, pp. 1971-1978.

International Search Report and Written Opinion for International Application No. PCT/US2019/025189, dated Jul. 2, 2019, 13 pages.

International Search Report and Written Opinion for International Application No. PCT/US2019/025202, dated Jul. 30, 2019, 13 pages.

International Search Report and Written Opinion for International Application Serial No. PCT/US2019/025194, dated Aug. 22, 2019, pp. 8.

International Search Report and Written Opinion for International Application Serial No. PCT/US2019/025211, dated Jul. 29, 2019, pp. 9.

International Search Report and Written Opinion for International Application Serial No. PCT/US2019/025218, dated Sep. 5, 2019, pp. 17.

International Search Report and Written Opinion for International Application Serial No. PCT/US2019/029956, dated Aug. 13, 2019, pp. 6.

International Search Report and Written Opinion for International Application Serial No. PCT/US2019/029973, dated Jul. 23, 2019, pp. 5.

Janina, Kluge, et al. "Inducible promoters and functional genomic approaches for the genetic engineering of filamentous fungi", Applied Microbiology and Biotechnology, vol. 102, (Jun. 2, 2018), XP036546152, Jun. 2, 2018, pp. 6357-6372.

Jayashree, Chakravarty, et al., "Solvent production by engineered Ralstonia eutropha: channeling carbon to biofuel", Applied Microbiology and Biotechnology, vol. 102, (Apr. 29, 2018), XP036507417, early online publication Apr. 29, 2018 5021-5031.

Jiachao, Zhu, et al., "Factors for promoting polyhydroxyalkanoate (PHA) synthesis in bio-nutrient-removal and recovery system" 4th International Conference on Environmental Systems Research (ICESR 2017) Conference paper, XP002792821, DOI: 10.1088/1755-1315/178/1/012021, cited as a P-document, but the conference was held in 2017, 2018, pp. 1-4.

Jillian, Marc, et al., "Over expression of GroESL in Cupriavidus necator for heterotrophic and autotrophic isopropanol production", Metabolic Engineering, vol. 42, XP085136193 2017, pp. 74-84.

Joris, Beld, et al., Evolution of acyl-ACP thioesterases and [beta]-ketoacyl-ACP synthases revealed by protein-protein Interactions Journal of Applied Phycology., vol. 26, No. 4 Nov. 22, 2013 1619-1629.

Justyna, Mozejko-Ciesielska, et al., "Bacterial polyhydroxyalkanoates: Still fabulous ?", Microbiological Research, vol. 192, XP029740446, and reference Horng 2016, pp. 271-282.

Kianoush, Khosravi-Darani, et al., Simulation of bioreactors for poly(3-hydroxybutyrate) production from natural gas Iranian Journal of Chemistry and Chemical Engineering, vol. 39, XP002792822, (Modeling of . . . ); online publication in date 2018, pp. 1-24.

Koller, et al., "Potential and Prospects of Continuous Polyhydroxyalkanoate (PHA)", Production Bioengineering, May 29, 2015, pp. 94-121.

Koller, M., "A review on established and emerging fermentation schemes for microbial production of polyhydroxyalkanoate (PHA) biopolyesters", Fermentation, vol. 4, (Apr. 23, 2018), XP002792757, early online publication Apr. 23, 2018, pp. 1-30.

(56) References Cited

OTHER PUBLICATIONS

Kunasundari, et al., "Revisiting the Single Cell Protein Application of Cupriavidus necator H16 and Recovering Bioplastic Granules Simultaneously", Plos One, vol. 8, No. Oct. 10, 2013, 15 pgs.

Makkar, et al., "*Cupriavidus necator* Gen. Nov., Sp. Nov.: A Nonobligate Bacterial Predator of Bacteria in Soil", International Journal of Systematic Bacteriology, vol. 37, No. 4, Oct. 1987, pp. 323-326.

Marika, Zlesack, et al., "Chimeric Fatty Acyl-Acyl Carrier Protein Thioesterases Provide Mechanistic Insight into Enzyme Specificity and Expression", Applied and Environmental Microbiology, vol. 84, No. 10, Mar. 16, 2018, pp. 12.

Martin, Koller, et al., "Continuous production mode as a viable process-engineering tool for efficient poly (hydroxyalkanoate) (PHA) bio-production", Chemical and Biochemical Engineering Quarterly, vol. 28, XP002792820, 2014, pp. 65-77.

Matthias, Raberg, et al., "Ralstonia eutropha H16 in progress: applications beside PHAs and establishment as production platform by advanced genetic tools", Critical Reviews in Biotechnology, vol. 38, (Dec. 12, 2017), XP002792845, early online publication Dec. 12, 2017, pp. 494-510.

Miglena, Manandhar, et al., "Pimelic acid, the first precursor of the B acillus subtilis biotin synthesis pathway, exists as the free acid and is assembled by fatty acid synthesis", Molecular Microbiology, vol. 104, No. 4, Mar. 3, 2017, pp. 595-607.

Raberg, et al., "A Closer Look on the Polyhydroxybutyrate-(PHB-) Negative Phenotype of Ralstonia Eutropha PHB-4", Plos One, vol. 9, No. 5, May 2014, pp. 1-11.

Robert, Haushalter W., et al., "Production of Odd-Carbon Dicarboxylic Acids in *Escherichia coli* Using an Engineered Biotin-Fatty Acid Biosynthetic Pathway", Journal of the American Chemical Society, vol. 139, No. 13, Mar. 21, 2017, pp. 4615-4618.

Russell, J.B., "The Energy Spilling Reactions of Bacteria and Other Organisms", Journal of Molecular Microbiology Biotechnology, vol. 13, No. 1, 2007, pp. 1-11.

Shively, J.M. et al., "Something From Almost Nothing: Carbon Dioxide Fixation in Chemoautotrophs", Annual Review of Microbiology, vol. 52, 1998, pp. 191-230.

Sillman, et al., "Isolation of Nonobligate Bacterial Predators of Bacteria from Soil", Canadian Journal of Microbiology, vol. 32, No. 9, 1986, pp. 760-762.

Swathi, Alagesan, et al., "Functional genetic elements for controlling gene expression in Cupriavidus necator H16", Applied and Environmental Microbiology, vol. 84, (Oct. 2018), XP055604488, Oct. 2018, pp. 1-17.

Zeph, et al., "Gram-Negative Versus Gram-Positive (Actinomycete) Nonobligate Bacterial Predators of Bacteria in Soil", Applied Environmental Microbiology, vol. 52, No. Oct. 4, 1986, pp. 819-823.

"Cupriavidus necator", Wikipedia, Retrieved from Internet URL: https://en.wikipedia.org/wiki/Cupriavidus_necator#:~:text=Cupriavidus%20necator%20is%20a%20hydrogen,a%20source%20of%20energy%20C., Feb. 25, 2021, 7 Pages.

Non Final Office Action received for U.S. Appl. No. 16/372,092, dated Mar. 4, 2021, 9 Pages.

"Aeration", Retrieved from Internet URL : https://www.clrblu.com/aeration/, 02 Pages, 2021.

Final Office Action received for U.S. Appl. No. 16/372,092, dated Jul. 26, 2021, 10 Pages.

Hensirisak et al. "Scale-Up of Microbubble Dispersion Generator for Aerobic Fermentation", Applied Biochemistry and Biotechnology vol. 101, 2002, pp. 211-227, 2002.

Kaster et al., "Increased Oxygen Transfer in a Yeast Fermentation Using a Microbubble Dispersion", Applied Biochemistry and Biotechnology vol. 24/25, 1990, pp. 469-484 , 1990.

"Aminotransferase class III-fold pyridoxal phosphate-dependent enzyme [Aquitalea denitrificans]", NCBI Reference Sequence: WP_159877958.1, Jan. 19, 2020, 1 page.

"Aminotransferase class III-fold pyridoxal phosphate-dependent enzyme [*Aquitalea* sp. LB_tupeE]", NCBI Reference Sequence: WP_178973970.1, Jul. 11, 2020, 1 page.

"Aminotransferase class III-fold pyridoxal phosphate-dependent enzyme [Chromobacterium haemolyticum]", NCBI Reference Sequence: WP_166453011.1, Apr. 6, 2020, 1 page.

"Aminotransferase class III-fold pyridoxal phosphate-dependent enzyme [Chromobacterium vaccinii]", NCBI Reference Sequence: WP_166440807.1, Apr. 6, 2020, 1 page.

"Aminotransferase class III-fold pyridoxal phosphate-dependent enzyme [Crenobacter sedimenti]", NCBI Reference Sequence: WP_163315775.1, Apr. 6, 2020, 1 page.

"Aminotransferase class III-fold pyridoxal phosphate-dependent enzyme [Neisseriaceae bacterium B2N2-7]", GenBank: MXR37125.1, Jan. 6, 2020, 2 pages.

"Aminotransferase class III-fold pyridoxal phosphate-dependent enzyme [Paludibacterium paludis]", NCBI Reference Sequence: WP_189532963.1, Sep. 28, 2020, 1 page.

"Aminotransferase class III-fold pyridoxal phosphate-dependent enzyme [*Paludibacterium* sp. dN 18-1]", GenBank: MTD33855.1, Nov. 24, 2019, 1 page.

"Aminotransferase class III-fold pyridoxal phosphate-dependent enzyme [Vogesella alkaliphila]", NCBI Reference Sequence: WP_189374996.1, Sep. 28, 2020, 1 page.

"Aminotransferase class III-fold pyridoxal phosphate-dependent enzyme [Vogesella fluminis]", NCBI Reference Sequence: WP_189352298.1, Sep. 28, 2020, 1 page.

"Aminotransferase class III-fold pyridoxal phosphate-dependent enzyme [Vogesella oryzae]", NCBI Reference Sequence: WP_174874069.1, Jun. 22, 2020, 1 page.

"Aspartate aminotransferase family protein [Aquitalea magnusonii]", NCBI Reference Sequence: WP_059287319.1, Dec. 31, 2020. 1 page.

"Aspartate aminotransferase family protein [Aquitalea magnusonii]", NCBI Reference Sequence: WP_089085350.1, Jul. 15, 2017, 1 page.

"Aspartate aminotransferase family protein [*Aquitalea* sp. FJL05]", NCBI Reference Sequence: WP_124643387.1, Apr. 12, 2019, 1 page.

"Aspartate aminotransferase family protein [*Aquitalea* sp. THG-DN7.12]", NCBI Reference Sequence: WP_137009623.1, Oct. 16, 2019, 1 page.

"Aspartate aminotransferase family protein [Chromobacterium amazonense]", NCBI Reference Sequence: WP_106076402.1, Mar. 16, 2018, 1 page.

"Aspartate aminotransferase family protein [Chromobacterium haemolyticum]", GenBank: OQS32233.1, Apr. 6, 2017, 2 pages.

"Aspartate aminotransferase family protein [Chromobacterium haemolyticum]", GenBank: OQS37730.1, Apr. 6, 2017, 2 pages.

"Aspartate aminotransferase family protein [Chromobacterium haemolyticum]", NCBI Reference Sequence: WP_043593957.1, Apr. 15, 2016, 1 page.

"Aspartate aminotransferase family protein [Chromobacterium haemolyticum]", NCBI Reference Sequence: WP_081556739.1, Apr. 8, 2017, 1 page.

"Aspartate aminotransferase family protein [Chromobacterium haemolyticum]", NCBI Reference Sequence: WP_081576047.1, Apr. 8, 2017, 1 page.

"Aspartate aminotransferase family protein [Chromobacterium haemolyticum]", NCBI Reference Sequence: WP_161523523.1, Oct. 5, 2020, 1 page.

"Aspartate aminotransferase family protein [Chromobacterium paludis]", NCBI Reference Sequence: WP_149295777.1, Oct. 5, 2020, 1 page.

"Aspartate aminotransferase family protein [Chromobacterium phragmitis]", NCBI Reference Sequence: WP_114062556.1, Dec. 20, 2020.

"aspartate aminotransferase family protein [*Chromobacterium* sp. ATCC 53434]", NCBI Reference Sequence: WP_101708025.1, Jan. 10, 2018.

"Aspartate aminotransferase family protein [*Chromobacterium* sp. LK11]", Ncbi Reference Sequence: WP_048412320.1, Apr. 15, 2016, 1 page.

"Aspartate aminotransferase family protein [*Chromobacterium* sp. LK1]", NCBI Reference Sequence: WP_048411976.1, Apr. 15, 2016, 1 page.

(56) References Cited

OTHER PUBLICATIONS

"Aspartate aminotransferase family protein [*Chromobacterium* sp. MWU13-2610]", NCBI Reference Sequence: WP_103321487.1, Jan. 31, 2018, 1 page.
"Aspartate aminotransferase family protein [*Chromobacterium* sp. MWU14-2602]", NCBI Reference Sequence: WP_103903523.1, Feb. 10, 2018, 1 page.
"Aspartate aminotransferase family protein [*Chromobacterium* sp. Panama]", NCBI Reference Sequence: WP_107799474.1, Apr. 25, 2018, 1 page.
"Aspartate aminotransferase family protein [Chromobacterium sphagni]", NCBI Reference Sequence: WP_071116856.1, Aug. 23, 2017, 1 page.
"Aspartate aminotransferase family protein [Chromobacterium subtsugae]", NCBI Reference Sequence: WP_047237256.1, Mar. 20, 2018, 1 page.
"Aspartate aminotransferase family protein [Chromobacterium subtsugae]", NCBI Reference Sequence: WP_047243213.1, Apr. 15, 2016, 1 page.
"Aspartate aminotransferase family protein [Chromobacterium subtsugae]", NCBI Reference Sequence: WP_047257673.1, Apr. 15, 2016, 1 page.
"Aspartate aminotransferase family protein [Chromobacterium vaccinii]", NCBI Reference Sequence: WP_046156378.1, Oct. 25, 2019, 1 page.
"Aspartate aminotransferase family protein [Chromobacterium vaccinii]", NCBI Reference Sequence: WP_104946997.1, Mar. 4, 2018, 1 page.
"Aspartate aminotransferase family protein [Chromobacterium violaceum]", NCBI Reference Sequence: WP_011135573.1, Jul. 28, 2019, 1 page.
"Aspartate aminotransferase family protein [Chromobacterium violaceum]", NCBI Reference Sequence: WP_048405256.1, Apr. 15, 2016, 1 page.
"Aspartate aminotransferase family protein [Chromobacterium violaceum]", NCBI Reference Sequence: WP_081573061.1, Apr. 8, 2017, 1 page.
"Aspartate aminotransferase family protein [Chromobacterium violaceum]", NCBI Reference Sequence: WP_152637556.1, Oct. 31, 2019, 1 page.
"Aspartate aminotransferase family protein [*Crenobacter* sp. GY 70310]", NCBI Reference Sequence: WP_136552942.1, Oct. 16, 2019, 1 page.
"Aspartate aminotransferase family protein [Gulbenkiania indica]", NCBI Reference Sequence: WP_055434103.1, May 14, 2017, 1 page.
"Aspartate aminotransferase family protein [Gulbenkiania mobilis]", NCBI Reference Sequence: WP_054286466.1, May 14, 2017, 1 page.
"Aspartate aminotransferase family protein [Paludibacterium purpuratum]", NCBI Reference Sequence: WP_133682408.1, May 12, 2019, 1 page.
"Aspartate aminotransferase family protein [Paludibacterium yongneupense]", NCBI Reference Sequence: WP_028535161.1, Apr. 15, 2016, 2 pages.
"Aspartate aminotransferase family protein [Pseudogulbenkiania ferrooxidans]", NCBI Reference Sequence: WP_008952788.1, Apr. 15, 2016, 2 pages.
"Aspartate aminotransferase family protein [Pseudogulbenkiania ferrooxidans]", NCBI Reference Sequence: WP_021478068.1, Apr. 15, 2016, 1 page.
"Aspartate aminotransferase family protein [*Pseudogulbenkiania* sp. MAI-1]", NCBI Reference Sequence: WP_024302818.1, Apr. 15, 2016, 2 pages.
"Aspartate aminotransferase family protein [*Pseudogulbenkiania* sp. NH8B]", NCBI Reference Sequence: WP_014087389.1, Apr. 15, 2016, 2 pages.
"Aspartate aminotransferase family protein [Pseudogulbenkiania subflava]", NCBI Reference Sequence: WP_085275708.1, Apr. 22, 2017, 1 page.
"Aspartate aminotransferase family protein [Vogesella indigofera]",NCBI Reference Sequence: WP_120809711.1, Nov. 4, 2018, 1 page.
"Aspartate aminotransferase family protein [Vogesella mureinivorans]", NCBI Reference Sequence: WP_147694092.1, Oct. 5, 2020, 1 page.
"Aspartate aminotransferase family protein [Vogesella perlucida]", NCBI Reference Sequence: WP_147687830.1, Oct. 5, 2020, 1 page.
"Aspartate aminotransferase family protein [*Vogesella* sp. EB]", NCBI Reference Sequence: WP_047966302.1, Apr. 15, 2016, 1 page.
"Aspartate aminotransferase family protein [*Vogesella* sp. LIG4]", NCBI Reference Sequence: WP_088967522.1, Jul. 11, 2017, 1 page.
"Aspartate aminotransferase family protein [Vogesella urethralis]", NCBI Reference Sequence: WP_144371715.1, Oct. 5, 2020, 1 page.
"Aspartate aminotransferase family protein [*Xenophilus* sp. AP218F]", NCBI Reference Sequence: WP_088737038.1, Jul. 3, 2017, 1 page.
"Crystal structure of the omega transaminase from Chromobacterium violaceum in complex with PMP", PDB: 6S4G_A, Dec. 1, 2020, 2 pages.
"Multispecies: aspartate aminotransferase family protein [Aquitalea]", NCBI Reference Sequence: WP_045848621.1, Apr. 15, 2016, 1 page.
"Multispecies: aspartate aminotransferase family protein [Aquitalea]", NCBI Reference Sequence: WP_103523625.1, Aug. 6, 2020, 1 page.
"Multispecies: aspartate aminotransferase family protein [Chromobacterium]", NCBI Reference Sequence: WP_019104435.1, Apr. 18, 2017, 1 page.
"Multispecies: aspartate aminotransferase family protein [Chromobacterium]", NCBI Reference Sequence WP_043572477.1, Apr. 15, 2016, 1 page.
"Multispecies: aspartate aminotransferase family protein [Chromobacterium]", NCBI Reference Sequence: WP_043629242.1, Oct. 31, 2016, 1 page.
"Multispecies: aspartate aminotransferase family protein [Chromobacterium]", WP_043638691.1, Nov. 11, 2020, 1 page.
"Multispecies: aspartate aminotransferase family protein [Microvirgula]", NCBI Reference Sequence: WP_028498438.1, Jul. 14, 2018, 1 page.
"TPA: aspartate aminotransferase family protein [Betaproteobacteria bacterium]", GenBank: HEL32111.1, Mar. 2, 2020, 1 page.
Alagesan, S, et al., "13C-assisted metabolic flux analysis to investigate heterotrophic and mixotrophic metabolism in Cupriavidus necator H16", Metabolomics, vol. 14, Issue 9, 2018, 9 pgs.
Anderson, A. J.., et al., "Occurrence, Metabolism, Metabolic Role, and Industrial Uses of Bacterial Polyhydroxyalkanoates", Microbiological Review, 54(4), 1990, pp. 450-472.
U.S. Appl. No. 16/372,072, Corrected Notice of Allowability dated Jan. 26, 2021, 2 pages.
U.S. Appl. No. 16/372,072, Non Final Office Action dated Mar. 6, 2020, 20 pages.
U.S. Appl. No. 16/372,072, Notice of Allowance dated Jul. 17, 2020, 11 pages.
U.S. Appl. No. 16/372,072, Notice of Allowance dated Dec. 16, 2020, 9 pages.
U.S. Appl. No. 16/372,072, Preliminary Amendment filed Jul. 30, 2019, 5 pages.
U.S. Appl. No. 16/372,072, Preliminary Amendment filed Aug. 14, 2019, 5 pages.
U.S. Appl. No. 16/372,072, Response filed Feb. 11, 2020 to Restriction Requirement dated Dec. 11, 2019, 7 pages.
U.S. Appl. No. 16/372,072, Response filed Jun. 8, 2020 to Non Final Office Action dated Mar. 6, 2020, 11 pages.
U.S. Appl. No. 16/372,072, Restriction Requirement dated Dec. 11, 2019, 9 pages.
U.S. Appl. No. 16/372,083, Non Final Office Action dated Apr. 27, 2021, 14 pages.
U.S. Appl. No. 16/372,083, Notice of Allowability dated Sep. 22, 2021, 5 pages.
U.S. Appl. No. 16/372,083, Notice of Allowance dated Aug. 31, 2021, 9 pages.

(56) References Cited

OTHER PUBLICATIONS

U.S. Appl. No. 16/372,083, Response filed Apr. 12, 2021 to Restriction Requirement dated Mar. 8, 2021, 8 pages.
U.S. Appl. No. 16/372,083, Response filed Jul. 27, 2021 to Non Final Office Action dated Apr. 27, 2021, 11 pages.
U.S. Appl. No. 16/372,083, Response filed Dec. 18, 2020 to Restriction Requirement dated Oct. 19, 2020, 7 pages.
U.S. Appl. No. 16/372,083, Restriction Requirement dated Mar. 8, 2021, 6 pages.
U.S. Appl. No. 16/372,083, Restriction Requirement dated Oct. 19, 2020, 8 pages.
U.S. Appl. No. 16/372,092, Advisory Action dated Oct. 7, 2021, 6 pages.
U.S. Appl. No. 16/372,092, Non Final Office Action dated Mar. 4, 2021, 9 pages.
U.S. Appl. No. 16/372,092, Response filed Jun. 2, 2021 to Non Final Office Action dated Mar. 4, 2021, 11 pgs.
U.S. Appl. No. 16/372,092, Response filed Dec. 17, 2020 to Restriction Requirement dated Oct. 21, 2020, 6 pages.
U.S. Appl. No. 16/372,092, Restriction Requirement dated Oct. 21, 2020, 7 pages.
U.S. Appl. No. 16/372,106, Final Office Action dated Oct. 4, 2021, 29 pages.
U.S. Appl. No. 16/372,106, Non Final Office Action dated Apr. 30, 2021, 26 pages.
U.S. Appl. No. 16/372,106, Response filed Jan. 19, 2021 to Restriction Requirement dated Dec. 28, 2020, 8 pages.
U.S. Appl. No. 16/372,106, Response filed Jun. 15, 2021 to Non Final Office Action dated Apr. 30, 2021, 12 pages.
U.S. Appl. No. 16/372,106, Restriction Requirement dated Dec. 28, 2020, 7 pages.
U.S. Appl. No. 16/398,351, Final Office Action dated Jul. 2, 2021, 24 Pages.
U.S. Appl. No. 16/398,384, Non Final Office Action dated Oct. 23, 2020, 13 pages.
U.S. Appl. No. 16/399,145, Advisory Action dated Feb. 1, 2021, 4 pages.
U.S. Appl. No. 16/399,145, Final Office Action dated Dec. 4, 2020, 17 pages.
U.S. Appl. No. 16/399,145, Non Final Office Action dated Jun. 17, 2021, 20 pages.
U.S. Appl. No. 16/399,145, Non Final Office Action dated Aug. 12, 2020, 16 pages.
U.S. Appl. No. 16/399,145, Response filed Jan. 25, 2021 to Final Office Action dated Dec. 4, 2020, 12 pages.
U.S. Appl. No. 16/399,145, Response filed Jun. 3, 2020 to Restriction Requirement dated Apr. 17, 2020, 7 pages.
U.S. Appl. No. 16/399,145, Response filed Sep. 15, 2021 to Non Final Office Action dated Jun. 17, 2021, 11 Pages.
U.S. Appl. No. 16/399,145, Response filed Nov. 6, 2020 to Non Final Office Action dated Aug. 12, 2020, 12 pages.
U.S. Appl. No. 16/399,145, Restriction Requirement dated Apr. 17, 2020, 9 pages.
U.S. Appl. No. 16/399,155, Advisory Action dated Jun. 1, 2020, 3 pages.
U.S. Appl. No. 16/399,155, Final Office Action dated Mar. 5, 2020, 23 pages.
U.S. Appl. No. 16/399,155, Non Final Office Action dated Feb. 16, 2021, 17 pages.
U.S. Appl. No. 16/399,155, Response filed May 5, 2020 to Final Office Action dated Mar. 5, 2020, 12 pages.
U.S. Appl. No. 16/399,155, Response filed May 14, 2021 to Non Final Office Action dated Feb. 16, 2021, 11 pages.
U.S. Appl. No. 16/399,155, Response filed Jun. 5, 2020 to Advisory Action dated Jun. 1, 2020, 13 pages.
U.S. Appl. No. 16/399,155, Response filed Jun. 5, 2020 to Final Office Action dated Mar. 5, 2020, 13 pages.

Bramer, C O., "The malate dehydrogenase of Ralstonia eutropha and functionality of the C(3)/C(4) metabolism in a Tn5-induced mdh mutant", FEMS Microbiol Letters, vol. 212, Issue 2, Jul. 2, 2002, pp. 159-164.
Brandt, U, et al., "Elevated poly(3-hydroxybutyrate) synthesis in mutants of Ralstonia eutropha H16 defective in popolysaccharide biosynthesis", Applied Microbiology and Biotechnology, 2012, vol. 95, 2012, pp. 471-483.
Brigham, C J., et al., "Correction for Whole-genome microarray and gene deletion studies reveal regulation of the polyhydroxyalkanoate production cycle by the stringent response in Ralstonia eutropha H16", Appl Environ Microbiol., vol. 83, Issue 15, 2017, pp. 1-2.
Brigham, C J., et al., "Whole-genome microarray and gene deletion studies reveal regulation of the polyhydroxyalkanoate production cycle by the stringent response in Ralstonia eutropha HI6", Appl Environ Microbial., vol. 78, Issue 22, 2012, pp. 8033-8044.
Brigham, C.J., et al., "Engineering Ralstonia eutropha for Production of Isobutanol from C02, H2 and 02", Advanced Biofuels and Bioproducts, (2013) Chapter 39, pp. 1065-1090.
Brown, D R., et al., "Nitrogen stress response and stringent response are coupled in *Escherichia coli*", Nature communications, 2014, vol. 5, 4115, , 8 pgs.
Bruland, et al., "Unravelling the C3/C4 carbon metabolism in Ralstonia eutropha H16", Journal of Applied Microbiology, 109, 2010, pp. 79-90.
Cavalheiro et al., "Poly(3-hydroxybutyrate) production by Cupriavidus necator using waste glycerol", Process Biochemistry, vol. 44, pp. 509-515 (2009).
Chen, R, et al., "A highly active decarboxylating dehydrogenase with rationally invelted coenzyme specificity", PNAS, vol. 92, Issue 25, 1996, pp. 11666-11670.
Chen, R, et al., "Redesigning secondary structure to invert coenzyme specificity in isopropylmalate dehyrogenase", PNAS, vol. 93, 1996, pp. 12171-12176.
Choi, J C., et al., "Modulation of 3-hydroxyvalerate molar fraction in poly(3-hydroxybutyrate-3-hydroxyvalerate) using Ralstonia eutropha transformant co-amplifying phbC and NADPH generation-related zwf genes", Enzyme and Microbial Technology, vol. 32, Issue 1, 2003, pp. 178-185 (Abstract Only).
Cramm, R. J., "Genomic view of energy metabolism in Ralstonia eutropha HI6", Journal of Molecular Microbiology and Biotechnology, vol. 16, 2009, pp. 38-52.
Deveraux, J., et al., "A comprehensive set of sequence analysis programs for the VAX", Nucleic Acids Research, 12 (1 Part 1), 1984, pp. 387-395.
Devos, et al., "Practical limits of function prediction", Proteins: Structure, Function, and Genetics vol. 41, 2000, pp. 98-107.
Ding, H, et al., "Glycerol utilization by Rhizobium leguminosarum requires an ABC transporter and affects competition for nodulation", Microbiology, vol. 158, 2012, pp. 1369-1378.
Doberstein, C., et al., "Polythioester synthesis in Ralstonia eutropha H16: novel insights into 3,3'-thiodipropionic acid and 3,3'-dithiodipropionic acid catabolism", Journal of Biotechnology, vol. 184, 2014, pp. 187-198 (Abstract Only).
Du, et al., "Effects of Environmental Conditions on Cell Growth and Poly-β-Hydroxybutyrate Accumulation in Alcaligenes eutrophus", World Journal of Microbiology & Biotechnology, vol. 16, 2000, pp. 9-13.
Gao, C, et al., "Lactate utilization is regulated by the FadR-type regulator LldR in Pseudomonas aeruginosa", Journal of Bacteriology, vol. 194, 2012, pp. 2687-2692.
Grousseau, et al., "Isopropanol Production with Engineered Cupriavidus necator as Bioproduction Platform", Appl. Microbial. Biotechnol., vol. 98, No. 9, 2014, pp. 4277-4290.
Gyaneshwar, et al., "Sulfur and Nitrogen Limitation in *Escherichia coli* K-12: Specific Homeostatic Responses", Journal of Bacteriology, vol. 187, No. 3, Feb. 2005, pp. 1074-1090.
Hauryliuk, V, et al., "Recent functional insights into the role of (p)ppGpp in bacterial physiology", Nature Reviews Microbiology, vol. 13, 2015, pp. 298-309.
Inoue, H, et al., "Biochemical and molecular characterization of the NAD(+)-dependent isocitrate dehydrogenase from the

(56) References Cited

OTHER PUBLICATIONS chemolithotrophAcidithiobacillus thiooxidans", FEMS Microbial Letters, vol. 214, Issue 1, 2002, pp. 127-132.
International Application Seria No. PCT/US2019/029795, Written Opinion dated Jul. 11, 2019, 6 pages.
International Application Serial No. PCT/US2019/025189, International Preliminary Report on Patentability dated Oct. 15, 2020, 9 pages.
International Application Serial No. PCT/US2019/025194, International Preliminary Report on Patentability dated Oct. 15, 2020, 15 pages.
International Application Serial No. PCT/US2019/025202, International Preliminary Report on Patentability dated Oct. 15, 2020, 12 pages.
International Application Serial No. PCT/US2019/025218, Invitation to Pay Additional Fees dated Jun. 25, 2019, 8 pages.
International Application Serial No. PCT/US2019/029795, International Preliminary Report on Patentability dated Nov. 3, 2020, 8 pages.
International Application Serial No. PCT/US2019/029795, International Search Report dated Jul. 11, 2019, 4 pages.
International Application Serial No. PCT/US2019/029798, International Preliminary Report on Patentability dated Nov. 3, 2020, 14 pages.
International Application Serial No. PCT/US2019/029798, International Search Report dated Sep. 12, 2019, 7 pages.
International Application Serial No. PCT/US2019/029798, Invitation to Pay Additional Fees dated Jul. 22, 2019, 16 pages.
International Application Serial No. PCT/US2019/029798, Written Opinion dated Sep. 12, 2019, 12 pages.
International Application Serial No. PCT/US2019/029817, International Preliminary Report on Patentability dated Nov. 3, 2020, 14 pages.
International Application Serial No. PCT/US2019/029817, International Search Report dated Sep. 23, 2019, 8 pages.
International Application Serial No. PCT/US2019/029817, Invitation to Pay Additional Fees dated Aug. 1, 2019, 15 Pages.
International Application Serial No. PCT/US2019/029817, Written Opinion dated Sep. 23, 2019, 12 pages.
International Application Serial No. PCT/US2019/029827, International Preliminary Report on Patentability dated Nov. 3, 2020, 14 pages.
International Application Serial No. PCT/US2019/029827, International Search Report dated Sep. 23, 2019, 9 pages.
International Application Serial No. PCT/US2019/029827, Invitation to Pay Additional Fees dated Jul. 23, 2019, 17 Pages.
International Application Serial No. PCT/US2019/029827, Written Opinion dated Sep. 23, 2019, 12 Pages.
International Application Serial No. PCT/US2019/029956, International Preliminary Report on Patentability dated Nov. 12, 2020, 12 pages.
International Application Serial No. PCT/US2019/029973, International Preliminary Report on Patentability dated Nov. 12, 2020, 12 pages.
International Preliminary Report on Patentability for PCT application No. PCT/US2019/025211, dated Oct. 15, 2020, 13 pages.
Ishii, et al., "Uniprot database", accession No. G2J4X6, 2011, 2 pages.
Ishizaki, et al., "Microbial production of poly-D-3-hydroxybutyrate from CO2", Appl. Microbiol. Biotechnol., vol. 57, 2001, pp. 6-12 (Abstract Only).
Ishizuka, H, et al., "Putrescine Oxidase of Micrococcus rubens: Primary Structure and *Escherichia coli*", Journal of General Microbiology, vol. 139, 1993, pp. 425-432.
Jones, G.W. and Kennedy, RE., "Prevention of Gas Explosions by Controlling Oxygen Concentration", Industrial and Engineering Chemistry, vol. 27, Issue 11, 1935, pp. 1344-1346.
Judger, B-E., et al., "An analysis of the changes in soluble hydrogenase and global gene expression in Cupriavidusnecator (Ralstonia eutropha) HI6 grown in heterotrophic diauxic batch culture", Microbial Cell Factories, vol. 14, 2015,pp. 1-11.
Juengert, J. R., et al., "Absence of ppGpp Leads to Increased Mobilization of Intermediately Accumulated Poly(3-Hydroxybutyrate) in Ralstonia eutropha HI6", Applied and Environmental Microbiology, vol. 83, Issue 13, 2017, pp. e00755-17 (1-16).
Kaddor, C, et al., "Effects of homologous phosphoenolpyruvate-carbohydrate phosphotransf erase system proteins on carbohydrate uptake and poly(3-ydroxybutyrate) accumulation in Ralstonia eutropha HI6", Appl. Environ. Microbial. vol. 77, 2011, pp. 3582-3590.
Kaddor, C, et al., "Implications of various phosphoenolpyruvate-carbohydrate phosphotransf erase system mutations on glycerol utilization and poly(3-hydroxybutyrate) accumulation in Ralstonia eutropha H16", AMB Express, vol. 1, 2011, pp. 16.
Karstens, K, et al., "Phosphotransferase protein EIIANtr interacts with SpoT, a key enzyme of the stringent response, in Ralstonia eutropha HI6", Microbiology, vol. 160, 2014, pp. 711-722.
Kazakov, A E., et al., "Comparative genomics of regulation of fatty acid and branched-chain amino acid utilization in proteobacteria". Journal of Bacteriology, vol. 191, 2009, pp. 52-64.
Kim, et al., "Effect of overexpression of Actinobacillus succinogenes phosphoenolpyruvate carboxykinase on succinate production in *Escherichia coli*", Appl Environ Microbial.70(2), Feb. 2004, pp. 1238-1241.
Kisselev, L, "Polypeptide Release Factors in Prokaryotes and Eukaryotes: Same Function, Different Structure", Structure vol. 10, 2002, pp. 8-9.
Kizer, et al., "Application of functional genomics to pathway optimization for increased isoprenoid production", Appl Environ Microbial 74(10) doi: 10.1128/AEM.02750-07. Epub Mar. 14, 2008, May 2008, pp. 3229-3241.
Klasson, K.T., et al.,"Bioreactor design for synthesis gas fermentations", Fuel, vol. 70, Issue 5, 1991, pp. 605-614.
Krausse, et al., "Essential role of the hprK gene inRalstonia eutropha HI6", J Mol Microbial Biotechnol, vol. 17, 2009, pp. 146-152.
Kyte, Jack, et al., "A Simple Method for Displaying the Hydropathic Charcter of a Protein", Journal of Molecular Biology, 157, 1982, pp. 105-132.
Lardi, M, et al., "σ-54-Dependent Response to Nitrogen Limitation and Virulence in Burkholderia cenocepacia Strain H111", Appl. Environ. Microbiol., vol. 81, Issue 12, 2015, pp. 4077-4089.
Lee, et al., "Microbial Production of Ethanol from Acetate by Engineered Ralstonia eutropha", Biotechnology and Bioprocess Engineering, vol. 21, 2016, pp. 402-407.
Lee, et al., "Regulation of poly-β-hydroxybutyrate biosynthesis by nicotinamide nucleotide in Alcaligene eutrophus", FEMS Microbiological letters, vol. 131, 1995, pp. 35-39.
Lee, J N., et al., "Metabolic Engineering of Pentose Phosphate Pathway in Ralsonia eutropha for Enhanced Biosynthesis of poly-β-hydroxybutyrate", Biotechnology Progress, vol. 19, Issue 5, 2003, pp. 1444-1449.
Lenczak, J. L., et al., "High cell density strategy for poly(3-hydroxybutyrate) production by Cupriavidus necator", Brazilian Journal of Chemical Engineering, vol. 28, Issue 4, 2011, pp. 585-596.
Leyn, et al., "Control of proteobacterial centralcarbon metabolism by the HexR transcriptionalregulator: a case study in Shewanella oneidensis", Journal of Biological Chemistry, vol. 286, Issue 41, 2011, pp. 35782-35794.
Leyn, S A., et al., "Comparative genomics and evolution of transcriptional regulons in Proteobacteria", Microbial Genomics, 2016, pp. 1-15.
Li, Z J., et al., "Overexpression of NAD kinase in recombinant *Escherichia coli* harboring the phbCAB operon improves poly(3-hydroxybutyrate) production", Appl Microbial Biotechnol., vol. 83, Issue 5, 2009, pp. 939-947.
Lin, S, et al., "Biotin Synthesis Begins by Hijacking the Fatty Acid Synthesis Pathway", Nature Chemical Biology, vol. 6, No. 9, Sep. 2010, pp. 682-688.
Liu, X, "Comparative analysis of genes frequently regulated by drugs based on connectivity map transcriptome data", PLoS One, vol. 12, Issue 6, 2017, pp. e0179037 (1-13).

(56) References Cited

OTHER PUBLICATIONS

Lu, et al., "Studies in the production of branched-chain alcohols in engineered Ralstonia eutropha", Bioenergy and Biofuels, 96, 2012, 283-297.
Lu, et al., "Studies on the Production of Branched-chain Alcohols in Engineered Ralstonia eutropha", Appl, Microbial, Biotechnol, vol. 96, No. 1, 2012, 15 pgs.
Lucas, et al., "Gen Bank accession No. ACU95033", Aug. 26, 2009, p. 1.
Maddipati, P., "Ethanol production from syngas by Clostridium strain P11 using com steep liquor as a nutrientreplacement to yeast extract", Bioresoure Technology, vol. 102, Issue 11, 2011, pp. 6494-6501.
March, J C., et al., "Expression of an anaplerotic enzyme, pyruvate carboxylase, improves recombinant protein production in *Escherichia coli*", Applied and Environmental Microbiology, vol. 68, Issue 11, 2002, pp. 5620-5624.
McKinlay, J. B., et al., "Carbon dioxide fixation as a central redox cofactor recycling mechanism in bacteria", PNAS, vol. 107, Issue 26, 2010, pp. 11669-11675.
Meng, J, et al., "High-yield anaerobic succinate production by strategically regulating multiple metabolic pathways pased on stoichiometric maximumin *Escherichia coli*", Microbial Cell Factories, vol. 15, 2016, 13 pgs.
Myers, Eugene, et al., "Optimal alignments in linear space", Computer Applications in the Biosciences, vol. 4, 1988, pp. 11-17.
Needleman, Saul, et al., "A general method applicable to the search for similarities in amino acid sequence of two proteins". Journal of Molecular Biology, vol. 48, Issue 3, 1970, pp. 443-453.
Non-Final office action received for U.S. Appl. No. 16/398,351, dated Feb. 1, 2021, 24 pages.
Non-Final office action received for U.S. Appl. No. 16/398,401, dated Feb. 16, 2021, 29 pages.
Non-Final Office Action received for U.S. Appl. No. 16/398,365, dated Jan. 25, 2021, 10 Pages.
Obruca, S, et al., "Application of random mutagenesis to enhance the production of polyhydroxyalkanoates by Cupriavidus necator H16 on waste frying oil", World J Microbiol Biotechnol, 2013, vol. 29, 2013, pp. 2417-2428.
Olaya-Abril, et al., "Poly(3-hydroxybutyrate) hyperproduction by a global nitrogen regulator NtrB mutant strain of Paracoccus denitrificans PD1222", FEMS Microbiology Letters, vol. 365:fnx251, 2008, 8 pgs.
Orita, L, et al., "Identification of mutation points in Cupriavidus necator NCIMB 11599 and genetic reconstitution of Glucose-utilization ability in wild strain H16 for polyhydroxyalkanoate production", Journal of Bioscience and Bioengineering, vol. 113, Issue 1, 2012, pp. 63-69
Papagiani, M, "Recent advances in engineering the central carbon metabolism of industrially important bacteria", Microbial Cell Factories, vol. 11, 2012, 13 pgs.
Park, J S., et al., "Metabolic Characteristics of Isocitrate Dehydrogenase Leaky Mutant of Alcaligene eutrophus and its Utilization for Poly-Hydroxybutyrate Production", Journal of Fermentation and Bioengineering, 1996, vol. 81, Issue 3, 1996, pp. 197-205.
Park, S, et al., "Oxaloacetate and malate production in engineered *Escherichia coli* by expression of codon-optimized phosphoenolpyruvate carboxylase2 gene from Dunaliella salina", Bioprocess Biosyst Eng., vol. 36 Issue 1, 2013, pp. 127-131 (Abstract Only).
Pearson, William R.., et al., "Improved tools for biological sequence comparison", Proc Natl Acad Sci USA, 85(8), 1988, pp. 2444-2448.
Persuhn, D C., et al., "The transcriptional activator NtrC controls the expression and activity of glutamine synthetase in Herbaspirillum seropedicae", FEMS Microbiology Letters, vol. 192, 2000, pp. 217-221.
Phillips, J.R., et al., "Syngas Fermentation: A Microbial Conversion Process of Gaseous Substrates to Various Products", Fermentation, vol. 3, Issue 2, 2017, pp. 26.
Pohlmann, A, et al., "Genome sequence of the bioplastic-producing "Knallgas" bacterium Ralsonia eutropha H16", Nature Biotechnology, vol. 24, No. 10, 2007, pp. 1257-1262.
Prather KLJ et al. De nova biosynthetic pathways: Rational design of microbial chemical factories. Current Opinion in Biotechnology, 2008. 19:468-474 (Year: 2008).
Przybylski, et al., "Synthesis of the Building Block 2-Hydroxyisobutyrate from Fructose and Butyrate by Cupriavidus necator H16", Appl, Microbial, Biotechnol, vol. 97, 2013, pp. 8875-8885.
Oi, et al., "Model-driven redox pathway manipulation for improved isobutanol production in Bacillus subtilis complemented with experimental validation and metabolic profiling analysis", PLoS One, vol. 9, Issue 4, e93815, 2014, pp. 1-11.
Raberg, M, "Ralstoni a eutropha H16 in progress: applications beside PHAs and establishment as production platform by advanced genetic tools", Critical Reviews in Biotechnology, vol. 38, Dec. 12, 2017, pp. 494-510 (Abstract Only).
Rosa, L T., et al., "Tripartite ATP-Independent Periplasmic (TRAP) Transporters and Tripartite Tricarboxylate Transporters (TIT): From Uptake to Pathogenicity", Frontiers in Microbiology, vol. 8,, 2018, 16 pgs.
Sacamboio, E. N. M., et al., "The transcriptional regulator NtrC controls glucose-6-phosphate dehydrogenase expression and polyhydroxybutyrate synthesis through NADPH availability in Herbaspirillum seropedicae", Scientific Reports, vol. 7, Article No. 13546, 2017, pp. 1-12.
Sadowski, M I., et al., "The sequence-structure relationship and protein function prediction", Current Opinion in Structural Biology 19, 2009, pp. 357-362.
Sanchez, A. M., et al., "Effect of overexpression of a soluble pyridine nucleotide transhydrogenase (UdhA) on the production of poly(3-hydroxybutyrate) in *Escherichia coli*", Biotechnol Prog., vol. 22, Issue 2, 2006, pp. 420-425 (Abstract Only).
Saur, U, et al., "The PEP-pyruvate-oxaloacetate node as the switch point for carbon flux distribution in bacteria", FEMS Microbiology Reviews, vol. 29, Issue 4, 2005, pp. 765-794.
Schlegel, H. G., et al., "Formation of the Dehydroganses for Lactate, Ethanol and Butanediol in the Strictly Aerobi Bacterium Alcaligene eutrophus", Microbiology, vol. 117, 1980, pp. 475-481.
Schobert, P, et al., "Unusual C3 and C4 metabolism in the chemo-autotroph Alcaligenes eutrophus", Journal of Bacterialogy, vol. 159, Issue 1, 1984, pp. 167-172.
Schramke, et al., "Revisiting Regulation of Potassium Homeostasis in *Escherichia coli*: The Connection to Phosphate Limitation", Wiley Microbiologyopen, vol. 6, No. 3, 2017, pp. 1-16.
Schwartz, E, et al., "A proteomic view of the facultatively chemolithoautotrophic lifestyle of Ralstonia eutropha H16", Proteomics, vol. 9, Issue 22, 2009, pp. 5132-5142 (Abstract Only).
Seffernick, J L., et al., "Melamine Deaminase and Atrazine Chlorohydrolase: 98 Percent Identical but Functionally Different", Journal of Bacteriology, 183, 2001, pp. 2405-2410.
Segura, D, et al., "Inactivation of pycA, encoding pyruvate carboxylase activity, increases polybeta-hydroxybutyrate accumulation in Azotobacter vinelandii on solid medium", Appl Microbial Biotechnol, pp. 65, Issue 4, 2004, pp. 414-418.
Sekar, B S., et al., "Co-production of hydrogen and ethanol from glucose in *Escherichia coli* by activation of pentose-phosphate pathway through deletion of phosphoglucose somerase (pgi) and overexpression of glucose-6-phosphate dehydrogenase (zwf) and 6-phosphogluconate", dehydrogenase ( gnd), Biotechnology for Biofuels, vol. 10, 85, 2017, 12 pgs.
Shang, et al., "Poly(3-hydroxybutyrate) Synthesis in Fed-batch Culture of Ralstonia eutropha with Phosphate Limitation Under Different Glucose Concentrations", Biotechnology Letters, vol. 25, Issue 17, 2003, pp. 1415-14197.
Shulman, Andrew, et al., "Structural Determinants of Allosteric Ligand Activation in RXR Heterodimers", Cell, vol. 116, 2004, pp. 417-429.
Sillman, et al., "Isolation of nonobligate bacterial predators of bacteria from soil", Canadian Journal of Microbiology, 32, 1986, pp. 760-762.
Singh, et al., "Protein Engineering Approaches in the Post-Genomic Era", Curr Protein Pept Sci., 2017, pp. 1-11.

(56) References Cited

OTHER PUBLICATIONS

Slabu, et al., "Discovery, Engineering and Synthetic Application of Transaminase Biocatalysts", ACS Catalysis 7, 2017, pp. 8263-8284.
Smith, Temple, et al., "Comparison of biosequences", Advances in Applied Mathematics, 2(4), Dec. 1981, pp. 482-489.
Steinbuchel, A, et al., "A multifunctional fermentative alcohol dehydrogenase from the strict aerobe Alcaligenes eutrophus: purification and properties", Eur J Biochem, vol. 141, Issue 3, 1984, pp. 555-564.
Stokke, R, et al., "Biochemical characterization of isocitrate dehydrogenase from Methylococcus capsulatus reveals a unique NAD+-dependent homotetrameric enzyme", Arch Microbial., vol. 187, Issue 5, 2007, pp. 361-370.
Sun, J, et al., "Involvement of glnB, glnZ, and glnD genes in the regulation of poly-3-hydroxybutyrate biosynthesis by ammonia in *Azospirillum brasilense* Sp7", Appl. Environ. Microbial, vol. 68, Issue 2, 2002, pp. 985-988.
Sun, J, et al., "The ntrB and ntrC genes are involved in the regulation of poly-3-hydroxybutyrate biosynthesis by ammonia in *Azospirillum brasilense* Sp7", Appl. Environ. Microbial., vol. 66, Issue 1, 2000, pp. 113-117.
Tan, Z, et al., "Activating phosphoenolpyruvate carboxylase and phosphoenolpyruvate carboxykinase in combination for improvement of succinate production", Appl. Environ. Microbial, vol. 79, Issue 16, 2013, pp. 4838-4844.
Tanaka, K. and Ishizaki, A., "Production of poly-d-3-hydroxybutyric acid from carbon dioxide by a two-stage culture method employing Alcaligenes eutrophus ATCC 17697T", Journal of Fermentation and Bioengineering, vol. 77, Issue 4, 1994, pp. 425-427.
Tang, et al., "Identification of Dehalobacter reductive Dehalogenases that catalyse dechlorination of chlorofom, 1,1,1-tricloroethane and 1,1-dicloroethane", Phil Trans R Soc B 368:Mar. 18, 2012, 2013, pp. 1-10.
U.S. Appl. No. 16/399,155, Response filed Oct. 15, 2019 to Non-Final Office Action dated Jul. 15, 2019, 12 pages.
Uniprot database, entry AOAOU2WHGO, Mar. 2016, 4 pages.
Valderrama, J A., et al., "AccR is a master regulator involved in carbon catabolite repression of the anaerobic catabolism of aromatic compounds in *Azoarcus* sp. CIB", Journal of Biological Chemistry, vol. 289, Issue 4, 2014, pp. 1892-1904.
Vemuri, G N., "Physiological response of central metabolism in *Escherichia coli* to deletion of pyruvate oxidase and introduction of heterologous pyruvate carboxylase", Biotechnology and Bioengineering, vol. 90, Issue 1, 2005, pp. 64-76.
Vollbrecht, D, et al., "Excretion of Metabolites by hydrogen Bacteria III. D(-)-3-hydroxybutanoate", European J. Appl. Microbiol. Biotechnol, vol. 7, 1979, pp. 259-266.
Vollbrecht, et al., "Excretion of Metabolites by Hydrogen Bacteria I. Autotrophic and Heterotrophic Fermentations", European journal of applied microbiology and biotechnology, vol. 6, Issue 2, 1978, pp. 145-155.
Vollbrecht, et al., "Excretion of Metabolites by Hydrogen Bacteria II. Influences of Aeration, pH, Temperature, and Age of Cells", European Journal of Applied Microbiology and Biotechnology, vol. 6, Issue 2, 1978, pp. 157-166.
Vollbrecht, et al., "Excretion of Metabolites by Hydrogen Bacteria IV. Respiration Rate-dependent Formation of Primary Metabolites and of Poly-3-Hydroxybutanoate", European Journal of Applied Microbiology and Biotechnology, vol. 7, Issue 3, 1979, pp. 267-276.
Volodina, E, et al., "Characterization of propionate GoA-transferase from Ralstonia eutropha H16", Appl Microbial, Biotechnol, vol. 98, Issue 8, 2014, pp. 3579-3589.
Wang, et al., "Poly(3-Hydroxybutyrate) Production with High Productivity and High Polymer Content by a Fed-Batch 23 Culture of Alcaligenes latus under Nitrogen Limitation", Applied and Environmental Microbiology, vol. 63, No. 9, Sep. 1997, pp. 3703-3706.

Wang, R, et al., "Isocitrate dehydrogenase from *Streptococcus mutans*: biochemical properties and evaluation of a putative phosphorylation site at Ser102", PLoS One, vol. 8, Issue 3, 2013, pp. e58918 (1-8).
Weinberg, Z, et al., "Identification of 22 candidate structured RNAs in bacteria using the Cmfinder comparative genomics pipeline", Nucleic Acids Research, vol. 35,, 2007, pp. 4809-4819.
Welden, et al., "Cation Transport in *Escherichia coli* Vii. Potassium Requirement for Phosphate Uptake", The Journal of General Physiology, vol. 50, No. 6, 1967, pp. 1641-1661.
Whisstock et al., "Prediction of protein function from protein sequence and structure", Quarterly Reviews of BioPhysics, vol. 36, Issue 3, pp. 307-340 (2003).
Winnen, B, et al., "The tripartite tricarboxylate transporter (TIT) family", Res. Microbial, vol. 154, Issue 7, 2003, pp. 457-465.
Witkowski, A, et al., "Conversion of a β-Ketoacyl Synthase to a Malonyl Decarboxylase by Replacement of the Active-Site Cysteine with Glutamine", Biochemistry, 38, 1999, pp. 11643-11650.
Wu, M-C, et al., "A Novel Type II NAD+-Specific Isocitrate Dehydrogenase from the Marine Bacterium Congregibacte itoralis KT71", PLoS One., vol. 10, Issue 5, 2015, pp. 1-17.
Youngquist, et al., "Functional Genomics Analysis of Free Fatty Acid Production under Continuous Phosphate Limiting Conditions", J. Ind. Microbial. Biotechnol., vol. 44, May 2017, pp. 759-772.
Zhang M et al. Propagated Perturbations from a Peripheral Mutation Show Interactions Supporting WW Domain Thermostablity, 2018, Structure. 26, 1474-1485. (Year: 2018).
U.S. Appl. No. 16/372,083, Supplemental Amendment filed for Non-Final Office Action dated Apr. 27, 2021, 8 pages.
Huang et al., "Bacterial and Yeast Cultures—Process Characteristics, Products, and Applications", Bioprocessing for Value-Added Products from Renewable Resources, pp. 185-223, Dec. 2007 (Year: 2007).
Non-Final Rejection received for U.S. Appl. No. 16/372,092, dated Nov. 26, 2021, 10 Pages.
Final Office Action received for U.S. Appl. No. 16/399,155, dated Jul. 28, 2021, 14 pages.
U.S. Appl. No. 16/372,092, Response filed Sep. 21, 2021 to Final Office Action dated Jul. 26, 2021, 11 pages.
Aspartate aminotransferase family protein [Rhodobacteraceae bacterium CH30], GenBank: RQW28969.1, Dec. 2, 2018, 2 pages.
Baltz et al. "Manual of Industrial Microbiology and Biotechnology", ASM Press, 2010, 4 Pages (Abstract).
Berg et al."Biochemistry 5th ed.", W H Freeman and Company, 2002, 1 Page (Abstract).
Bramer, C.O. et al. "Putative lyase protein", Gen Bank Q2Z1A9, Retrieved from Internet URL: https://www.ncbi.nlm.nih.gov/protein/122559031?sat=35&satkey=13062155, Oct. 31, 2006, 01 page.
Database UniProt, "RecName: Full=Thiopurine S-methyltransferase [ECO:0000256|HAMAPRule:MF_00812, ECO:0000256|SAAS:SAAS00896910}; EC=2.1.1.67{ECO:0000256|HAMAP-Rule:MF_00812, ECO:0000256|SAAS:SAAS00896910}; AltName: Full= Thiopurine methyltransferase {ECO: 0000256|HAMAP-Rule:MF_00812}", EBI accession No. UNIPROT:A0A1 L8MA47 Database accession No. A0A1L8MA47, Mar. 15, 2017, 04 Pages.
Database UniProt, "SubName: Full=Acyl-ACP thioesterase {ECO:0000313| EMBLCDD77481.1}", retrieved from EBI accession No. EBI accession No. UNIPROT:R7CHF5 Database accession No. R7CHF5, Jul. 24, 2013, 03 Pages.
Database UniProt,"RecName: Full=Thiopurine S-methyltransferase [ECO:0000256|HAMAPRule:MF_00812, ECO:0000256|SAAS:SAAS00896910}; EC=2.1.1.67{ECO:0000256|HAMAP-Rule:MF_00812, ECO:0000256|SAAS:SAAS00896910}; AltName: Full= Thiopurine methyltransferase {ECO: 0000256|HAMAP-Rule:MF_00812}" ,EBI accession No. UNIPROT:A0A009ZVV4 Database accession No. A0A009ZVV4, Jun. 11, 2014, 04 Pages.
Final office action received for U.S. Appl. No. 16/398,351, dated Feb. 28, 2022, 11 pages.
Harder et al., "Physiological responses to nutrient limitation", Annual Review of Microbiology, vol. 37, 1983, pp. 1-23.

(56) References Cited

OTHER PUBLICATIONS

Katalin Kovacs et al: Metabolic engineering of Cupriavidus necator H16 for the sustainable production of C3 and C5 monomers and polymers, CInet Conference 4, Jan. 20-23, 2019 Conference paper, 1 Page, retrieved on Jun. 30, 2022 (Abstract).
KEGG Enzyme 1.6.1.1. Retrieved Feb. 22, 2022 (Year: 2022) pp. 1-2.
KEGG Enzyme 1.6.1.2. Retrieved Feb. 22, 2022 (Year: 2022) pp. 1-2.
KEGG Enzyme 7.1.1.1. Retrieved Feb. 22, 2022 (Year: 2022) pp. 1-2.
Kihlberg,"The Microbe as a Source of Food" Annual Review of Microbiology, vol. 26, 1972, pp. 427-466.
Inui, M., et al., Metabolic Engineering of Corynebacterium glutamicum for Fuel Ethanol Production under Oxygen Deprivation Conditions. 2004. J. Mol. Microbiol. Biotechnol., vol. 8, pp. 243-254.
Non-Final Rejection received for U.S. Appl. No. 16/398,401, dated Nov. 9, 2021, 38 Pages.
Pohlmann A. et al. " Pyruvate carboxylase Cupriavidus necator H16", Gen Bank Q0KC80, Retrieved from Internet URL: https://www.ncbi.nlm.nih.gov/protein/Q0KC80, Nov. 28, 2006, 02 pages.
Pohlmann A. et al., "Phosphoenolpyruvate carboxykinase Cupriavidus necator H16", Gen Bank Q0K5F4, Retrieved from Internet URL: https://www.ncbi.nlm.nih.gov/protein/123133475?sat=35&satkey=13483043, Nov. 28, 2006, 01 page.
Pohlmann A. et al., "Phosphoenolpyruvate carboxykinase Cupriavidus necator H16", Gen Bank Q0K7M4, Retrieved from Internet URL: https://www.ncbi.nlm.nih.gov/protein/123133692?sat=35&satkey=13483220, Nov. 28, 2006, 01 page.
Stanbury et al. "Principles of Fermentation Technology", 3rd Edition, Aug. 31, 2016, 4 Pages.(Abstract).
U.S. Appl. No. 16/372,083, Preliminary Amendment filed on Jul. 30, 2019, 4 pages.
U.S. Appl. No. 16/399,155, Non Final Office Action dated Jul. 15, 2019, 19 pages.
Folsom, J.P. et al., "Physiological and Proteomic Analysis of *Escherichia coli* Iron-Limited Chemostat Growth," Journal of Bacteriology, vol. 196, No. 15, pp. 2748-2761 (Aug. 2014).

\* cited by examiner

METHODS FOR CONTROLLING OXYGEN CONCENTRATION DURING AEROBIC BIOSYNTHESIS

CROSS REFERENCE TO RELATED APPLICATION

The present application claims the benefit of U.S. Provisional Patent Application No. 62/650,585 filed Mar. 30, 2018, which is incorporated herein by reference for all purposes.

FIELD

The present disclosure generally relates to methods for controlling oxygen concentration during aerobic biosynthesis. In particular, the present disclosure relates to methods for decreasing oxygen concentration below the limiting oxygen concentration ("LOC") in the gaseous phase of a fermentation broth containing a flammable gas such as hydrogen before the gaseous phase separates from the fermentation broth.

BACKGROUND

In gas fed fermentation, carbon-rich gases such as carbon dioxide, carbon monoxide and methane, are converted by microorganisms into a wide range of products such as fuel, protein, and chemical compounds, for example, alcohols and organic acids. These products are used by industries in the chemical, petrochemical, pharmaceutical, animal feed, environmental and agricultural sectors. Gas fermentation processes may utilize a variety of feedstocks including domestic, industrial, or agricultural waste, thereby reducing reliance on fossil sources of carbon and reducing emission of greenhouse gases. The fermentation process generally operates at lower reaction temperatures and pressures when compared to high temperature and pressure chemical catalytic reactions.

Microorganisms used in the fermentation process grow under various engineering and physical conditions inside the fermenter such as agitation, mixing, aeration, pressure, shear, temperature, and pH. Some microorganisms grow under anaerobic conditions while others grow under aerobic conditions. For aerobic reactions, air is generally used as the source of oxygen, but oxygen-enriched air or pure oxygen can also be used. It is generally preferable to operate at the highest possible oxygen concentration to maximize oxygen mass transfer and thereby optimize productivity. This is because the rate of oxygen mass transfer from the gas phase to the liquid phase is the rate-limiting step for most aerobic microbial biosynthetic reactions.

During aerobic biosynthesis, any unreacted oxygen from the oxygen source, e.g., air, separates from the fermentation broth into the headspace of the bioreactor, e.g., fermenter. The unreacted oxygen mixes with other unreacted gases, e.g., effluent gases, in the headspace of the bioreactor. In certain situations where the feed gas contains potentially flammable components, the sum of the feed gases, e.g., an oxygen-containing gas, a hydrogen-containing gas, and a carbon-dioxide-containing gas, can have an oxygen concentrations greater than the LOC for the composition containing said flammable components e.g., 6 vol. % oxygen concentration for an air/hydrogen system. Any unreacted oxygen in the gaseous mixture in the fermenter headspace and effluent gases may result in flammable mixtures especially when flammable gases (e.g., hydrogen), flammable volatile organic products, or intermediates, are used or produced in the aerobic biosynthesis process. Even when operating at small-scale, e.g., the laboratory, there is still a risk of explosions from the flammable gas mixture, but the extent this risk is mitigated due to the small-scale of the bioreactor and reduced gas volumes. However, when scaling up the size of bioreactors for pilot or commercial use, the risk of flammability and explosion is a major concern for safe operation of the process. Moreover, when designing a large-scale system to operate above the LOC, necessary equipment design features can be extremely capital expensive especially at higher operating pressures, e.g., explosive-proof electronics, explosive-proof valves, thicker steel, etc. can be required.

Therefore, the need exists for improved control of the oxygen concentration below the limiting oxygen concentration (LOC) for flammability of flammable gas components before the gaseous phase separates from the fermentation broth into the headspace of the bioreactor while achieving acceptable productivity, capital cost (capital efficiency), and operating cost.

SUMMARY

In some embodiments, the present disclosure is related to a method for controlling oxygen concentration during aerobic biosynthesis including: feeding an oxygen-containing gas into a bioreactor including a fermentation feedstock; reacting the fermentation feedstock with the oxygen-containing gas to form a broth including a gaseous phase dispersed within the broth, the gaseous phase comprising unreacted oxygen from the oxygen-containing gas; reducing the concentration of the unreacted oxygen in the gaseous phase to less than the limiting oxygen concentration ("LOC") for flammability; and separating the gaseous phase from the broth. In some aspects, the step of reducing the concentration of the unreacted oxygen occurs prior to the step of separating the gaseous phase from the broth. In some aspects, the step of reducing the concentration of the unreacted oxygen in the gaseous phase comprises adsorbing or reacting the unreacted oxygen with an oxygen reduction catalyst. In some aspects, the step of reducing the concentration of the unreacted oxygen in the gaseous phase comprises absorbing the unreacted oxygen in an oxygen-absorbing liquid that is separated from the fermentation broth with a liquid impervious gas membrane. In some aspects, the step of reducing the concentration of the unreacted oxygen in the gaseous phase comprises diluting the unreacted oxygen with a dilution agent. In some aspects, the dilution agent comprises a gas stream comprising one or more of nitrogen, carbon dioxide, and hydrogen. In some aspects, the dilution agent comprises less than 5 vol. % of oxygen, e.g., less than 3 vol. %. In some aspects, the oxygen-containing gas is air. In some aspects, the oxygen-containing gas comprises an oxygen concentration of greater than 21 vol. %. In some aspects, the gaseous phase separated from the broth comprises less than 6 vol. %, e.g., less than 5.5 vol. %, less than 5 vol. %, less than 4.5 vol. %, less than 4 vol. %, less than 3.5 vol. %, less than 3 vol. %, less than 2 vol. %, or less than 1 vol. %, of oxygen. In some aspects, the feedstock comprises a microorganism including *C. necator* or *C. metallidurans*. In some aspects, the bioreactor is selected from the group consisting of a single fermenter, multiple fermenters in series, a stirred-tank fermenter, a non-stirred tank fermenter, a membrane fermenter, a fixed-bed fermenter, a fluidized-bed fermenter, a single autoclave, multiple autoclaves in series, a plug flow fermenter, a pneumatically agitated fermenter, a gas-lift fermenter with an external loop having forced-circulation, a bubble-column fermenter, a fixed (packed) bed column fermenter, a horizontal single fermenter with multiple compartments, and multistage column fermenters. In some aspects, the gaseous phase is separated from the broth to a headspace of the bioreactor. In some aspects, the method further comprises feeding a flammable gas into the bioreactor. In some aspects, the flammable gas comprises hydrogen.

In some embodiments, the present disclosure is related to a method for controlling oxygen concentration during aerobic biosynthesis including: feeding a fermentation feedstock into a bioreactor comprising a microorganism; feeding a flammable gas into the bioreactor; feeding an oxygen-containing gas into the bioreactor, the oxygen-containing gas comprising an oxygen concentration greater than 21 vol. %; reacting the fermentation feedstock with the oxygen-containing gas and the flammable gas to form a broth including a gaseous phase dispersed within the broth, the gaseous phase comprising unreacted oxygen from the oxygen-containing gas and/or the flammable gas; reducing the concentration of the unreacted oxygen in the gaseous phase to less than the limiting oxygen concentration ("LOC"); and separating the gaseous phase from the broth to an upper headspace of the bioreactor. In some aspects, the flammable gas comprises hydrogen. In some aspects, the oxygen-containing gas and the flammable gas are continuously fed to the bioreactor in separate feeds. In some aspects, the step of reducing the concentration of the unreacted oxygen in the gaseous phase comprises adsorbing or reacting the unreacted oxygen with an oxygen reduction catalyst or absorbing the unreacted oxygen with an oxygen-absorbing liquid that is separated from the fermentation broth with a liquid impervious gas membrane. In some aspects, the step of reducing the concentration of the unreacted oxygen in the gaseous phase comprises diluting the unreacted oxygen with a dilution agent comprising less than 5 vol. % of oxygen, e.g., less than 3 vol. %.

BRIEF DESCRIPTION OF THE FIGURES

The present disclosure will be better understood in view of the appended non-limiting figures, in which.

DETAILED DESCRIPTION

Figure 1:
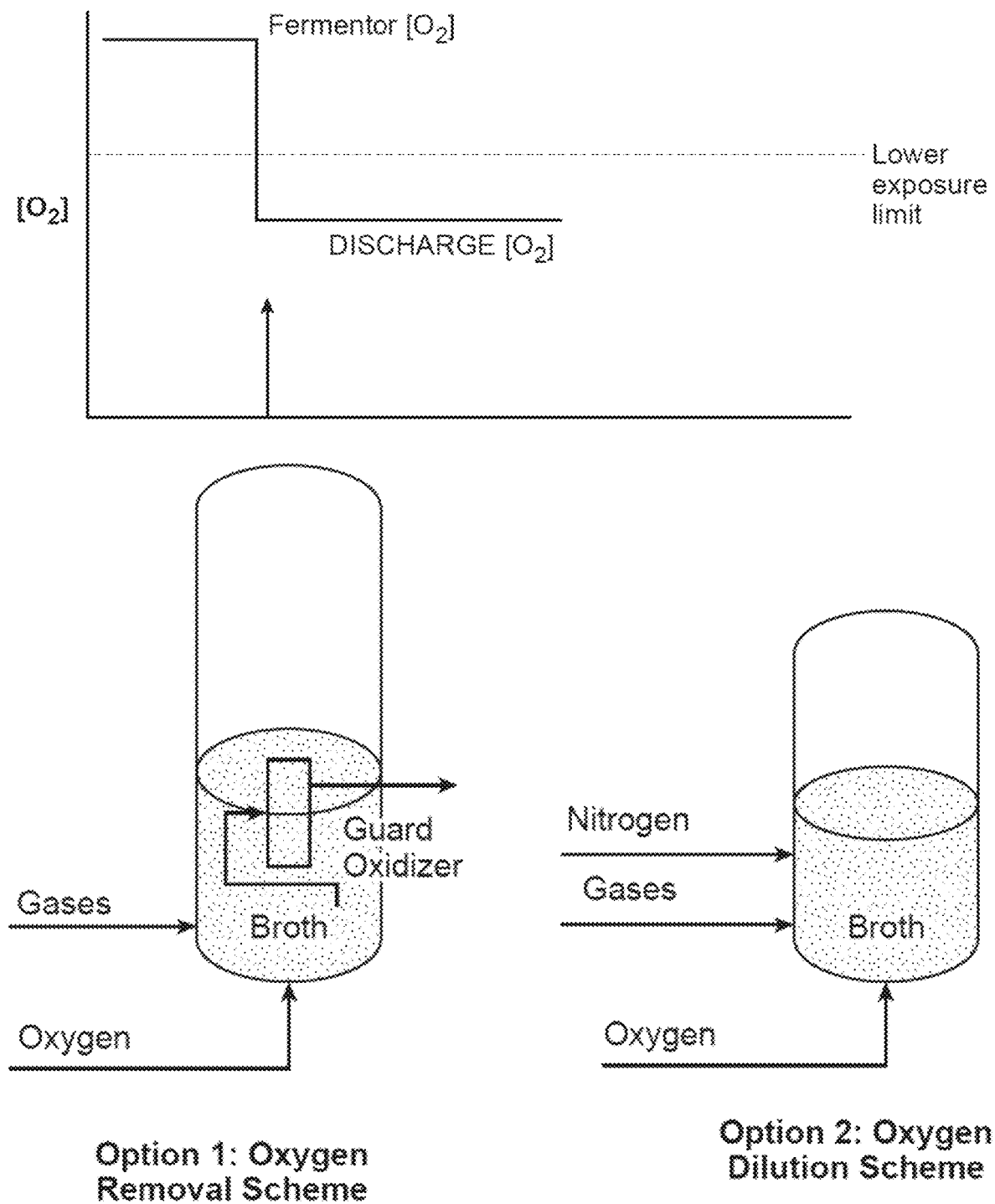
FIG. 1 shows a graph of decreased oxygen concentration in the effluent by either an oxygen destruction scheme (Option 1) or an oxygen dilution scheme (Option 2) in accordance with embodiments of the present disclosure.

The present disclosure is related to methods for controlling oxygen concentration during aerobic biosynthesis, e.g., fermentation. In some aspects, the oxygen concentration in the gaseous phase of the fermentation broth is reduced below the LOC of the flammable gaseous composition, e.g., 6 vol. % for a hydrogen/oxygen mixture, before it separates from the fermentation broth to the headspace of a bioreactor, e.g., a fermenter. The method for controlling oxygen concentration during aerobic biosynthesis may comprise feeding an oxygen-containing gas into a bioreactor including a microorganism and a flammable fermentation feedstock, and reacting the oxygen of the oxygen-containing gas with the microorganism to form a broth including a gaseous phase with unreacted oxygen dispersed within the broth. The gaseous phase dispersed within the broth can also include a flammable gas, e.g., at least a portion of the flammable fermentation feedstock. The method further includes reducing the concentration of the unreacted oxygen in the dispersed gaseous phase to less than the LOC before separating the gaseous phase from the fermentation broth to the headspace of the bioreactor.

Control Parameters for Oxygen Concentrations

As described herein, oxygen concentration in the bioreactor is controlled to be within specified ranges. The dissolved oxygen concentration in the fermentation broth is controlled to be at least a minimum value required for the microorganism to function. The minimum value is required because the microorganism is aerobic and requires a certain amount of oxygen. The concentration of gaseous oxygen in the headspace of the bioreactor is controlled to operate safely below the LOC utilizing the oxygen controlling schemes mentioned above. In some aspects, the LOC is approximately 6.0 vol. % oxygen in the gaseous mixtures outside of the fermentation broth. As a safety measure, the gaseous oxygen concentration in the headspace may be measured and controlled to be less than 90% of the LOC, e.g., less than 85%, less than 80%, less than 75%, or less than 70%. In some aspects, the gaseous oxygen concentration in the headspace is controlled to be in range from 60% to 95% of the LOC, e.g., from 65% to 90%, from 70% to 85%, from 70% to 80%, or from 75% to 85%.

The at least one feed stream comprising oxygen-containing gas may be introduced into the bioreactor by a suitable device in order to create microbubbles and enhance the gas-liquid interface between gas phase and bulk liquid. Additionally, gas-liquid mass transfer depends on the reactor configuration. There are seven general steps of mass transfer of the gases to the reaction site.

1. Diffusion through the bulk gas within a gas bubble to the gas-liquid interface.
2. Movement across the gas-liquid interface.
3. Diffusion of the solute gas through the relatively unmixed liquid region (film) adjacent to the bubble and into the well-mixed bulk liquid.
4. Transport of the solute gas through the bulk liquid to the stagnant film surrounding the cells.
5. Transport through the second unmixed liquid film associated with the cells.
6. Transport across the cell membrane.
7. Transport through the cell to the reaction site.

Gaseous Oxygen Concentration in Headspace

The upper limit for gaseous oxygen concentration in the headspace of the bioreactor is limited by safety considerations. Typically, the literature quotes a ratio of 7:1:1 or 8:1:1 for $H_2/CO_2/O_2$ (hydrogen/carbon dioxide/oxygen) for the initial gas mixture for optimum growth/production conditions for gas fermentation for C. necator (Ishizaki et al. 2001), although this ratio may vary due to adjustments and/or reaction needs. This means that the hydrogen/oxygen ratio is within the flammable range for hydrogen and oxygen gas concentrations. The critical oxygen concentration when mixed with hydrogen with carbon dioxide as a diluent is 5.9 vol. % (Jones and Kenny, 1935). Therefore, the LOC of 5.9 vol. % is here defined to be the minimum oxygen concentration at which a flammable gaseous mixture may form with fermentation process mixtures according to the present disclosure. These fermentation process includes a gaseous phase including, for example, oxygen, nitrogen, hydrogen, carbon dioxide and water vapor mixture, which rises to the headspace of the bioreactor, e.g., fermenter. Temperature and pressure conditions in the bioreactor may also influence the relative concentration of components in the headspace.

Before the gaseous phase in the fermentation broth rises to the headspace of the bioreactor, the unreacted components, e.g., oxygen, nitrogen, hydrogen, carbon dioxide and/or water vapor, are in a dispersed gaseous phase (e.g., gas bubbles) within the fermentation broth. The concentration of the oxygen in the dispersed gaseous phase is reduced below the LOC before it separates from the fermentation broth into the headspace of the reactor and mixes with other flammable gases. In particular, the oxygen concentration in the gaseous phase is reduced below the LOC of the headspace gaseous mixture, e.g., 6.0 vol. % oxygen. In order to maintain a safety margin, the bioreactor may be operated within 65% to 85% of the LOC, or even less than 65%. In some aspects, the gaseous oxygen concentration in the headspace is controlled to be from 3.5 to 4.5 vol. % oxygen, e.g., from 3.75 to 4.25 vol. %, from 3.85 to 4.15 vol. %, from 3.95 to 4.05 vol. %, or approximately 4 vol. % oxygen. The bioreactor effluent gas also has the same LOC.

In some aspects, the steps of mass transfer of the gases to the reaction site include diffusion through the bulk gas within gas bubbles to the gas-liquid interface, movement across the gas-liquid interface, diffusion of the solute gas through the relatively unmixed liquid region (film) adjacent to the bubble and into the well-mixed bulk liquid, transport of the solute gas through the bulk liquid to the stagnant film surrounding the cells, transport through the second unmixed liquid film associated with the cells, transport across the cell membrane, and transport through the cell to the reaction site.

The gas-liquid mass transfer also depends on the fermenter configuration and the gas mixture should be introduced into the fermenter by a suitable device to create small gas bubbles or microbubbles (having high specific surface area) and thereby increase the gas-liquid interfacial surface area available for gas mass transfer. It is desirable to operate at the highest possible oxygen concentration in order to maximize oxygen mass transfer and thereby maximize productivity in the gas fermentation reaction in the fermenter.

In some aspects, the concentration of unreacted oxygen in the gaseous phase is reduced by adsorbing or reacting the unreacted oxygen with an oxygen reduction catalyst. The oxygen reduction catalyst can be fed or present in the top of the bioreactor in a sufficient quantity to reduce the oxygen concentration in the gaseous phase below the LOC. In some aspects, the oxygen reduction catalyst is a solid oxygen reduction catalyst. The solid oxygen reduction catalyst can be provided in a portion of the bioreactor that is within or above the fermentation broth, e.g., immediately above or adjacent to the fermentation broth, to capture any unreacted oxygen before the separate gas phase forms in the headspace and of the bioreactor. In this way, the bulk gas only forms in the headspace after the gaseous phase of the fermentation broth comes into contact with the reaction zone of the solid oxygen reduction catalyst.

In some aspects, the concentration of the unreacted oxygen in the gaseous phase is reduced by adsorbing the unreacted oxygen with a liquid impervious gas membrane. The liquid impervious gas membrane includes an oxygen-absorbing liquid zone that prevents the broth and oxygen-absorbing liquid from co-mixing but allows the gas, e.g., from the collapsing gas bubbles in the broth, to escape from the broth through the membrane into the liquid zone. In other words, the liquid impervious gas membrane allows gas to pass through but is impervious to liquid. The liquid impervious gas membrane can be provided in a portion of the bioreactor that is immediately above or adjacent to the fermentation broth to capture any unreacted oxygen before the separate gas phase, e.g., bulk gas phase, forms in the headspace of the bioreactor. As used herein, the "headspace" is a portion of the bioreactor that does not include the fermentation broth, e.g., the volume above the fermentation broth in a vertical bioreactor. In some aspects, the oxygen dilution scheme and/or the oxygen removal (e.g., destruction) scheme is particularly suitable for use in a vertical reactor with a gradient of oxygen concentration, e.g., loop, uplift, or tubular reactor with a vertical separation area.

In some aspects, the concentration of the unreacted oxygen in the gaseous phase is reduced by diluting the gaseous phase including the unreacted oxygen with a dilution agent. The dilution agent may comprise a low oxygen gas stream that is fed into the bioreactor in a sufficient quantity to reduce the concentration of unreacted oxygen in the gaseous phase below the LOC of the flammable gas components. In some aspects, the dilution agent can be one or more of nitrogen, carbon dioxide, and hydrogen. In some aspects, the dilution agent comprises oxygen at a concentration below the LOC of the oxygen/flammable gas mixture.

Conventionally, in order to safely operate an aerobic microbial biosynthesis process with an explosive headspace or gas volume, e.g., gas fermentation, bioreactors are designed with stronger walls to withstand the pressure and temperature from deflagration or explosion. In some cases, the walls of the bioreactor may be reinforced, e.g., constructed with a larger width or made from a specific material, to withstand deflagration or explosion. However, utilizing fermenters with stronger walls may increase capital equipment cost and operating costs. Additional strategies include remaining below the flammability limit, separating flammable gases from oxygen, generating hydrogen in-situ, or directly using electrons as an energy source. However, these alternative strategies all have disadvantages in terms of economics or productivity, and may not be compatible with microorganisms for fermentation. For example, operating the bioreactor below the LOC would reduce oxygen mass transfer from the gas phase to the liquid phase and decrease the overall production rate of the end product.

The inventors have now discovered that decreasing the oxygen concentration in the fermentation broth prior to the gaseous phase separating from the fermentation broth can greatly reduce the flammability of the headspace gas and effluent gas while maintaining high oxygen mass transfer in the fermentation broth. Utilizing an oxygen removal scheme or an oxygen dilution scheme prior to the gaseous phase separating from the fermentation broth reduces the unreacted oxygen concentration below the flammability limit thereby enabling safe operation of the process. It was found that diluting the gaseous phase with an inert gas, e.g., nitrogen, to an oxygen concentration below the LOC can prevent deflagration or explosions in the headspace of the bioreactor. Advantageously, by diluting the gaseous phase late in the fermentation process, e.g., after the microorganism consumes the maximum amount of oxygen, the process maintains the maximum amount of oxygen in the fermentation broth before it separates to the headspace of the bioreactor. It was also found that removing oxygen from the gaseous phase by adsorption or absorption, e.g., using an oxygen reduction catalyst or oxygen-absorbing liquid in conjunction with a liquid impervious gas membrane, can also prevent deflagration or explosions in the headspace of the bioreactor. Beneficially, this also allows the bioreactor design to include a variety of materials, and is not limited to current reinforced bioreactor designs which accommodate controlled explosions.

The method advantageously controls the oxygen concentration in the fermentation broth to ensure safe operation of the bioreactor while maintaining oxygen concentration for high conversion of carbon-sources by microorganisms. In a typical gas fermentation process, a fermentation feedstock, e.g., gaseous CO2, including a microorganism is mixed with a flammable gas, e.g., hydrogen, and an oxygen-containing gas to form a fermentation broth. The flammable gas and the oxygen-containing gas are in a dispersed gaseous phase, e.g., gas bubbles, in the broth and any unreacted gases eventually rise to the headspace of the bioreactor, e.g., fermenter, as an effluent gas. The "effluent gas" refers to a gaseous mixture of the gases separated from the fermentation broth during the fermentation process. If the oxygen concentration is relatively high, e.g., above the limiting oxygen concentration ("LOC") for the flammable components in the effluent gas then it is susceptible to combustion. Advantageously, the process reduces the amount of oxygen in the dispersed gaseous phase before it rises to the upper portion, e.g., the headspace, of the bioreactor to prevent combustion. The present method enables using higher concentrations of excess oxygen in the feed streams to the bioreactor, e.g., above the LOC for the flammable components, to promote higher reaction rates and then either diluting or removing oxygen from the dispersed gaseous phase of the fermentation broth before it separates to form the bulk gas in the headspace of the bioreactor.

The present method can greatly improve process efficiencies and enable safe operation of a fermentation process. The method utilizes an oxygen-containing gas having a high oxygen concentration above the LOC, e.g., greater than 6 vol. % oxygen in a hydrogen/air mixture, to promote reaction with the microorganism, and then provides a means to remove or dilute the unreacted oxygen prior to the gaseous phase separating from the broth into the headspace. In some aspects, the oxygen-containing gas may comprise greater than 6 vol. % of oxygen, e.g., greater than 10 vol. %, greater than greater than 20 vol. %, greater than 40 vol. %, greater than 60 vol. %, greater than 80 vol. %, greater than 90 vol. %, greater than 95 vol. %, and greater than 99 vol. %. In some aspects, the oxygen-containing gas comprises pure oxygen.

In some cases, the fermentation process is an air fed fermentation reaction with an aerobic microorganism in a large-scale non-stirred fermenter. The large-scale non-stirred fermenter can include a fermentation broth with a dispersed gaseous phase within the flammability range. The oxygen concentration of the dispersed gaseous phase within the broth is decreased prior to the gaseous phase separating from the broth into the fermenter headspace. The oxygen concentration in the gaseous phase is decreased to a concentration below the LOC for flammability of the flammable components. For example, for a hydrogen-rich stream containing hydrogen concentrations above the lower flammability limit of hydrogen, the oxygen concentration in the gaseous phase is reduced to less than 6 vol. % of oxygen in the dispersed gaseous phase of the fermentation broth. In some aspects, oxygen concentration in the gaseous phase of the fermentation broth is reduced to less than 6 vol. % of oxygen, e.g., less than 5.9 vol. %, less than 5.5 vol. %, less than 5.0 vol. %, less than 4.0 vol. %, less than 3.0 vol. %, less than 2.0 vol. %, less than 1.0 vol. %, less than 0.5 vol. %, less than 0.1 vol. %, less than 0.01 vol. %. In some aspects, the oxygen concentration in the gaseous phase is controlled to be less than 90% of the LOC for flammability of the gaseous mixture in the headspace, e.g., less than 85%, less than 80%, less than 75%, or less than 70%.

Microorganism

A microorganism is provided to the bioreactor described herein in order for the aerobic biosynthesis, e.g., fermentation, to occur. For aerobic reactions, air is generally used as the source of oxygen, but oxygen-enriched air or pure oxygen can also be used. It is generally preferable to operate at the highest possible oxygen concentration in the dispersed gas phase within a fermenter to maximize oxygen mass transfer and thereby optimize productivity. This is because the rate of oxygen mass transfer from the gas phase to the liquid phase is a known rate-limiting step for most aerobic microbial biosynthetic reactions. A consequence of having oxygen concentrations higher than the LOC for the gaseous composition containing the flammable components, e.g., greater than 6 vol. % oxygen, is that any unreacted oxygen in the fermenter headspace and effluent gas stream can result in the formation of unsafe flammable mixtures when flammable gases (e.g., hydrogen), flammable volatile organic products, or intermediates are present.

The microorganism may be *Cupriavidus necator* (*C. necator*) or an organism with properties similar thereto. *C. necator* (previously called *Hydrogenomonas eutrophus, Alcaligenes eutropha, Ralstonia eutropha*, and *Wautersia eutropha*) is a Gram-negative, flagellated soil bacterium of the Betaproteobacteria class. This hydrogen-oxidizing bacterium is capable of growing at the interface of anaerobic and aerobic environments and easily adapts between heterotrophic and autotrophic lifestyles. Sources of energy for the bacterium include both organic compounds and hydrogen. Additional properties of *C. necator* include microaerophilicity, copper resistance (Makar and Casida; 1987), bacterial predation (Byrd et al., 1985; Sillman & Casida, 1986; Zeph & Casida, 1986) and polyhydrobutyrate (PHB) synthesis. In addition, the cells have been reported to be capable of both aerobic and nitrate dependent anaerobic growth. A non-limiting example of a *C. necator* organism useful in the present disclosure is a *C. necator* of the H16 strain. In one non-limiting embodiment, a *C. necator* host of the H16 strain with at least a portion of the phaC1AB1 gene locus knocked out (AphaCAB), as described in U.S. patent application Ser. No. 15/717,216, teachings of which are incorporated herein by reference, is used. The organism may be selected from non-pathogenic members of the genera *Ralstonia, Wausteria, Cupriavidus, Alcaligenes, Burkholderia* or *Pandoraea*.

Feed Streams

As described above, oxygen is needed for fermentation to occur and is introduced to the bioreactor via a feed stream. In order to introduce gaseous feed streams into the bioreactor in a safe manner, at least two different continuous streams of feeds are used. At least one continuous feed stream comprises a flammable gas (e.g., hydrogen) and at least one continuous feed stream comprises gaseous oxygen, e.g., an oxygen-containing gas. The at least one continuous stream comprising a flammable gas would comprise the hydrogen gas (flammable gas), may optionally comprise oxygen at a concentration below the limiting oxygen concentration ("LOC") for flammability of that gas stream, and may optionally comprise all or a portion of the CO$_2$ gas feed. The at least one continuous stream comprising gaseous oxygen may be an air feed stream. Such a stream would not contain hydrogen gas above the lower flammability limit of hydrogen but may optionally comprise all or a portion of the $CO_2$ gas feed. Each gas feed stream is introduced into the bioreactor by means such as microbubble generators, venturi nozzles, or porous gas spargers. By separating the hydrogen and oxygen into separate feed streams, a flammable gas mixture cannot form in the feed system and gas mixtures containing both hydrogen and oxygen are present only in the small-volume gas bubbles within the fermentation broth and within the headspace and effluent gas stream.

In some aspects, the oxygen-containing gas, e.g., air, can be fed directly into the fermentation broth. In some aspects, the oxygen-containing gas can be an oxygen-enriched source, e.g., oxygen-enriched air or pure oxygen. In some aspects, the oxygen-containing gas may comprise greater than 6 vol. % of oxygen, e.g., greater than 10 vol. %, greater than 20 vol. %, greater than 40 vol. %, greater than 60 vol. %, greater than 80 vol. %, or greater than 90 vol. %. In some aspects, the oxygen-containing gas may be pure oxygen.

In the fermentation process, air is generally used as the source of oxygen, but in some cases pure oxygen or oxygen-enriched air can be used. Any unreacted oxygen (along with the nitrogen present in the air) leaves the reactor or reactors in the gaseous effluent. The unreacted oxygen is commonly referred to as oxygen concentration in the effluent gas or "oxygen leakage." Any vaporized products in the gaseous effluent can be condensed and recovered, and the off-gases leave the system to an abatement system. Products remaining in the broth can be recovered from the liquid effluent from the bioreactor.

Bioreactor

As described herein, the temperature and pressure parameters of the bioreactor may vary, e.g., at pressures from below atmospheric pressure to above atmospheric pressure, and at temperatures from 20 to 50° C. The type of bioreactor to be used may be selected based on the desired operating temperature and pressure, as well as on additional factors. Examples of the additional factors include whether mechanical agitation or stirring is desirable, whether the microorganism will be immobilized, and how many oxygen addition points are desired. Examples of bioreactors, such as types of gas fermenters include single fermenters, multiple fermenters in series, stirred-tank fermenters, non-stirred-tank fermenters, membrane fermenters, fixed-bed fermenters, fluidized-bed fermenters, single autoclaves, multiple autoclaves in series, plug flow fermenters, pneumatically agitated fermenters such as gas (air)-lift fermenters, with either internal draft tube loop or external loop, gas-lift fermenters with external loop having forced-circulation, bubble-column fermenters, fixed (packed) bed column fermenters, horizontal single fermenters with multiple compartments, and multistage column fermenters. Additionally, fermenters can be operated in batch, fed-batch, and continuous mode.

Removing Oxygen from Fermentation Broth

As described herein, the fermentation broth comprises the feed streams in combination with the aerobic microorganism in the bioreactor. In some aspects, the feed streams, e.g., the carbon source feed stream, flammable gas-containing stream, and the oxygen-containing gas feed stream, react with the microorganism in the bioreactor to at least partially form the fermentation broth (which may also include other products, byproducts, and other media fed to the bioreactor). The unreacted oxygen, or the oxygen that is not consumed by the microorganism, exists as both dissolved oxygen and gaseous oxygen in a dispersed gaseous phase within the fermentation broth. The same holds true for the other gases that are soluble. The dispersed gaseous phase, containing the unreacted components, e.g., oxygen, nitrogen, hydrogen, carbon dioxide and/or water vapor, rises to the headspace of the bioreactor.

The concentration of oxygen in the gaseous phase is reduced to less than less than the limiting oxygen concentration ("LOC") for flammability of the flammable components in the dispersed gas composition. As a safety measure, the gaseous phase that rises to the headspace can be measured and controlled to be less than 90% of the LOC, e.g., less than 85%, less than 80%, less than 75%, or less than 70% of the LOC. In some aspects, the gaseous oxygen concentration in the headspace is controlled to be in range from 60% to 95% of the LOC, e.g., from 65% to 90%, from 70% to 85%, from 70% to 80%, or from 75% to 85%. In some aspects, the LOC should be less than 6.0 vol. % of oxygen, e.g., less than 5.9 vol. %, less than 5.5 vol. %, less than 5.0 vol. %, less than 4.0 vol. %, less than 3.0 vol. %, less than 2.0 vol. %, less than 1.0 vol. %, less than 0.5 vol. %, less than 0.1 vol. %, less than 0.01 vol. %, or alternatively, no oxygen. In certain aspects, hydrogen is the only flammable gas in the fermentation reaction system. In terms of ranges, the concentration of oxygen in the gaseous phase is reduced to a range from 0.01 vol. % to 6.0 vol. %, e.g., 0.1 vol. % to 5.9 vol. %, 0.5 vol. % to 5.5 vol. %, 1.0 vol. % to 5.0 vol. %, 2.0 vol. % to 4.0 vol. %, or 3.0 vol. % to 4.0 vol. %.

FIG. 1 shows a graph of decreased oxygen concentration in the gaseous phase in accordance with embodiments of the present disclosure. During fermentation, the oxygen concentration in the fermentation broth may be greater than the LOC, e.g., 6 vol. % of oxygen for a hydrogen/oxygen mixture. Since the rate of oxygen mass transfer from the gas phase to the liquid phase is the rate-limiting step in the fermentation process, it is generally preferable to supply the fermentation with the highest possible gas phase oxygen concentration to maximize oxygen mass transfer and thereby optimize production of the end product. However, when the gaseous phase of the fermentation broth includes high concentrations of oxygen, this can result in an effluent gas mixture in the headspace of the bioreactor that is a flammable mixture. In certain aspects, the sum of the feed gases into the fermentation broth is greater than the LOC. In some aspects, the present process reduces the oxygen concentration in the dispersed gaseous phase below the LOC, or to a safety margin below the LOC, before it separates from the broth and forms the effluent gases.

The oxygen concentration in the gaseous phase can be reduced by either an oxygen removal scheme or an oxygen dilution scheme in accordance with embodiments of the present disclosure. In each of these processes, the oxygen concentration of the dispersed gaseous phase is reduced before it separates from the fermentation broth as effluent gases in headspace of the bioreactor. Specifically, the oxygen concentration of the dispersed gaseous phase is reduced below the LOC, or a safety margin below the LOC, thereby preventing deflagration or explosions in the bioreactor when the separate gaseous phase mixture forms the effluent gases. As shown in FIG. 1, the oxygen concentration is reduced by employing an oxygen removal scheme (Option 1) or an oxygen dilution scheme (Option 2) prior to the gaseous phase separating from the fermentation broth.

In some aspects, the method of decreasing the oxygen content may comprise an oxygen removal scheme (Option 1). The oxygen removal scheme may comprise removing oxygen from the gaseous phase by adsorption or absorption. In some aspects, an oxygen reduction catalyst is fed into the fermentation broth before the gaseous phase separates from the broth. In some aspects, the oxygen reduction catalyst is a fixed bed installed in a portion of the bioreactor. In some aspects, the fixed bed including the oxygen reduction catalyst is located within, or immediately above, or adjacent to the fermentation broth such that a separate bulk gas phase does not form until above the oxygen reduction catalyst. In some aspects, the oxygen reduction catalyst is located at an interface between the fermentation broth and the headspace. In some aspects, the oxygen reduction catalyst is a solid oxygen reduction catalyst. The solid oxygen reduction catalyst can capture any unreacted oxygen before it mixes with effluent gas in the headspace of the bioreactor.

In some aspects, the oxygen removal scheme comprises a guard oxidizer for decreasing oxygen levels where potentially flammable gas or vapor mixtures are present. Guard oxidizers are disclosed, for example, in U.S. Pat. Nos. 6,888,034 and 9,221,737, and U.S. Patent Publication No. 2016/0176813, which are incorporated herein by reference. The guard oxidizer can be employed with the bioreactor, e.g., within the bioreactor, to reduce the oxygen concentration below a safety margin of the LOC. In some aspects, the guard oxidizer is within, immediately above, or adjacent to the fermentation broth to reduce the oxygen in the gaseous phase before it forms the bulk gas in the headspace of the bioreactor. In some aspects, the guard oxidizer can decrease oxygen content in the gaseous phase of the fermentation broth, the mixture of effluent gases in the headspace, and/or the final off-gas in an aerobic biosynthesis process. Any unreacted oxygen (along with the nitrogen present in the air) leaves the fermenter or fermenters in the gaseous effluent. In addition to decreasing oxygen concentration, the guard oxidizer also provides stability to the process.

Unfortunately, at oxygen leakage concentration in excess of the limiting oxygen concentration ("LOC"), unsafe flammable mixtures can form in the headspace and effluent gas stream. Therefore, as a margin of safety, the oxygen leakage for a hydrogen containing mixture is usually kept below 4 vol. %. Higher oxygen leakage also means that the air being fed to the fermenter(s) is not being fully utilized. In other words, the process requires more air, which leads to increased compression cost. In addition, an increased volume of off-gas causes increased cost for off-gas treatment. U.S. Pat. No. 3,957,876 (Rapoport & White) teaches a method to reduce oxygen leakage from a cyclohexane oxidation process through the use of a so-called clean up reaction zone.

Figure 2:
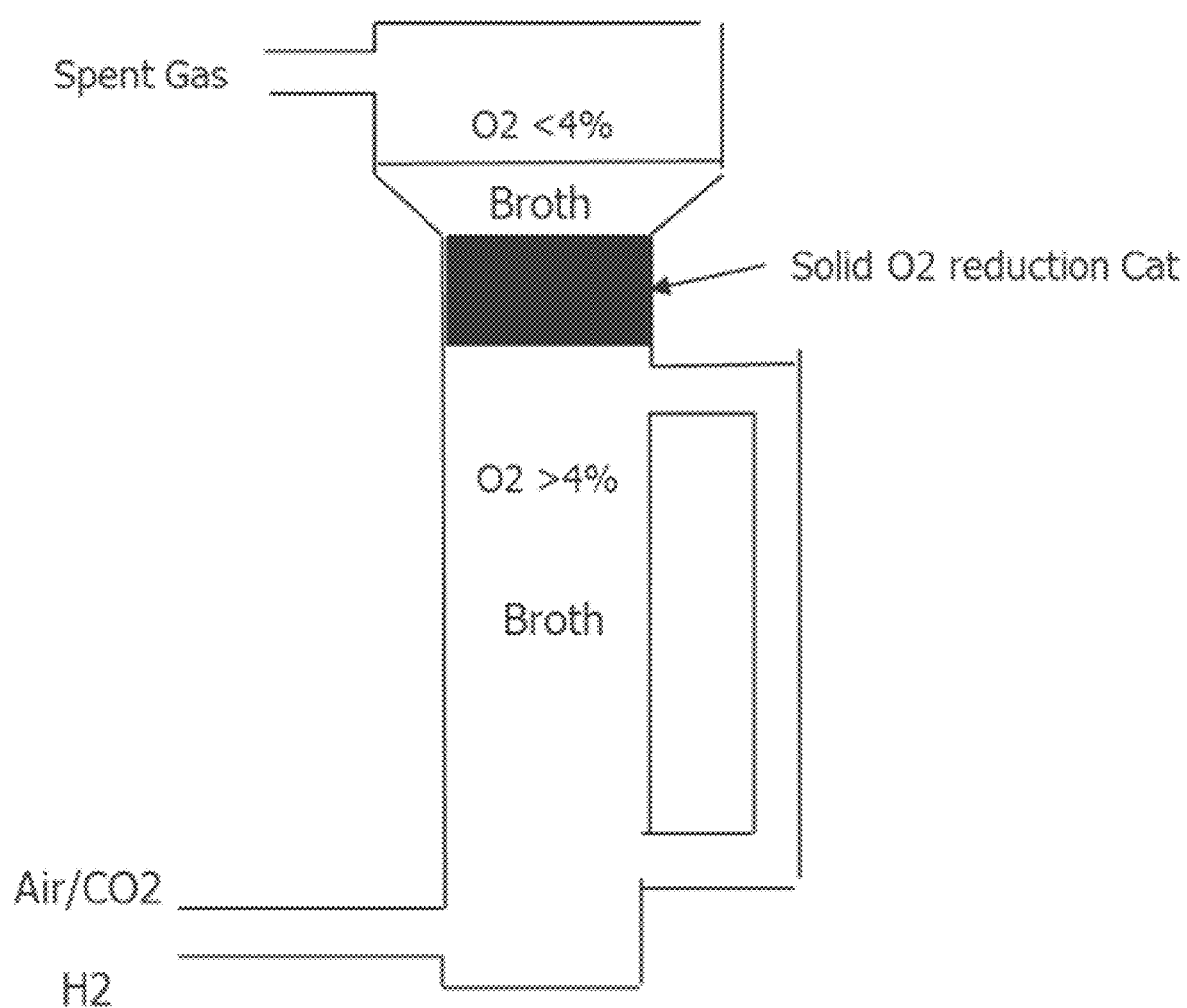
FIG. 2 shows an oxygen destruction scheme using a solid oxygen reduction catalyst in accordance with embodiments of the present disclosure.

FIG. 2 shows an oxygen removal scheme utilizing an oxygen reduction catalyst in accordance with embodiments of the present disclosure. The oxygen reduction catalyst reduces the oxygen concentration from greater than from 4.0 vol. % in the dispersed gaseous phase to less than 4.0 vol. % before the gaseous phase separates from the broth. FIG. 2 shows that the separated gaseous phase in the headspace of the bioreactor has an oxygen concentration less than 4.0 vol. %. In some aspects, the oxygen reduction catalyst reduces the oxygen concertation to a safety margin that is less than 80% of the LOC. In situations where air is utilized as the oxygen-containing gas, unreacted $H_2$, unreacted $CO_2$, nitrogen (from air) and water vapor (saturation concentration) will also be present in the effluent gas. The oxygen reduction catalyst can reduce the concentration of oxygen to less than 4.0 vol. %, which is less than 80% of the LOC for flammability.

In the illustrated embodiment, the oxygen-containing gas stream, e.g., air, is added to the bioreactor at the highest possible oxygen concentrations in order to maximize oxygen mass transfer and thus maximize productivity. However, unreacted oxygen can be removed from the unreacted gases leaving the fermenter as a gaseous effluent using a solid oxygen reduction catalyst. The solid oxygen reduction catalyst can be located in an upper portion of the fermentation broth to remove excess oxygen before the separate effluent gas phase forms in the headspace. In some aspects, the solid oxygen reduction catalyst is located at an interface between the fermentation broth and the headspace of the bioreactor.

Figure 3:
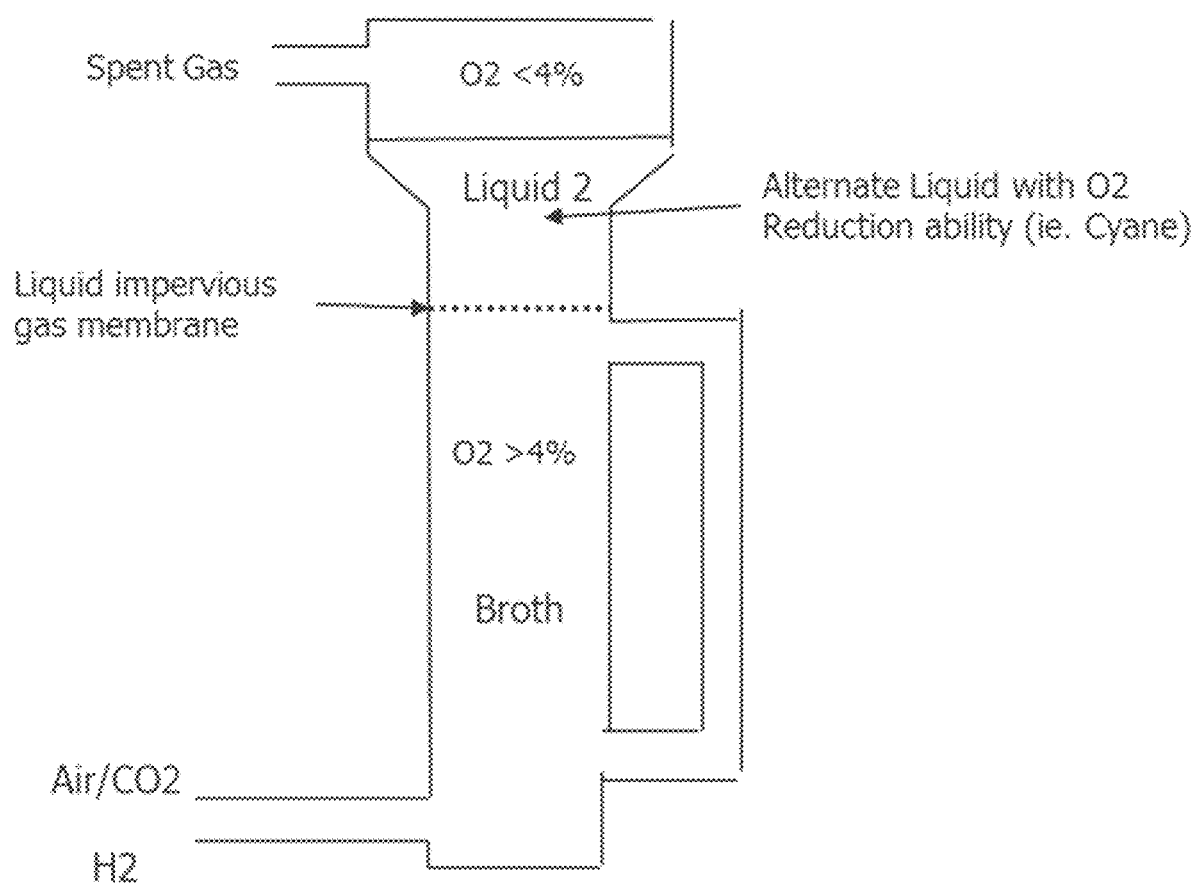
FIG. 3 shows an oxygen destruction scheme using a liquid impervious gas membrane in accordance with embodiments of the present disclosure.

FIG. 3 shows an oxygen removal scheme utilizing an oxygen-absorbing liquid, that is separated from the fermentation broth with a liquid impervious gas membrane, to reduce the oxygen concertation in the gaseous phase of the broth below the LOC in accordance with embodiments of the present disclosure. The liquid impervious gas membrane reduces the oxygen concentration from greater than from 4.0 vol. % in the dispersed gaseous phase to less than 4.0 vol. %. In some aspects, liquid impervious gas membrane reduces the oxygen concentration in gaseous phase by a relative amount greater than 5%, e.g., greater than 10%, greater than 20%, greater than 40%, greater than 60%, greater than 80%, or greater than 90%. The liquid impervious gas membrane may be located at an upper portion of the fermentation immediately above (adjacent to) the broth, e.g., a reaction zone for capturing the oxygen in the membrane. In some aspects, the liquid impervious gas membrane is located at an interface between the fermentation broth and the headspace of the bioreactor.

The liquid impervious gas membrane provides a reaction zone comprising an oxygen-absorbing liquid to remove oxygen from the gaseous phase. The liquid impervious gas membrane prevents the broth and oxygen-absorbing liquid from co-mixing, but allows the gas (from the collapsing gas bubbles in the broth) to escape from the broth into the liquid zone.

Figure 4:
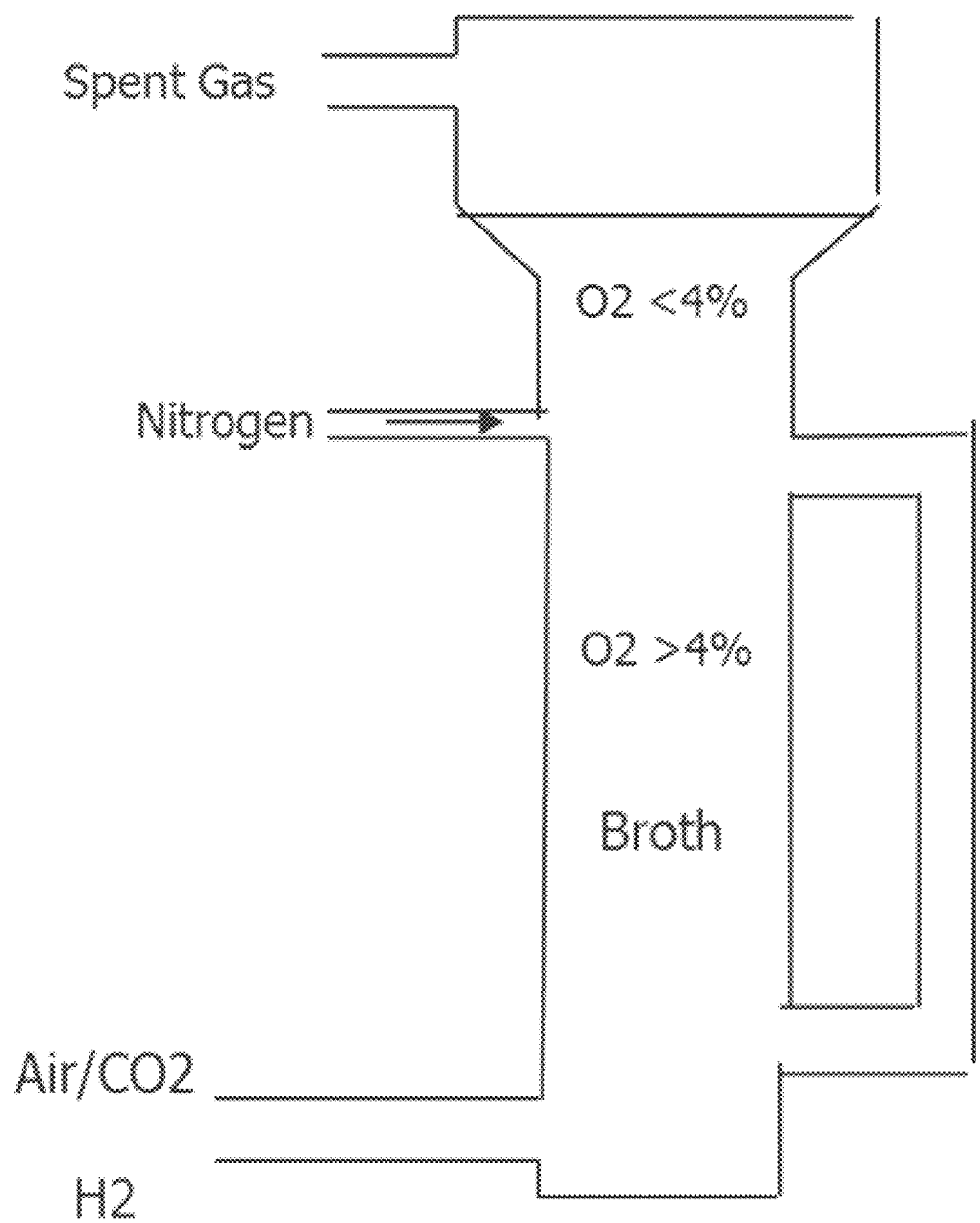
FIG. 4 shows an oxygen gas dilution scheme in which the dispersed gas phase within the fermenter is diluted with nitrogen to reduce the oxygen concentration below the LOC in the dispersed gaseous phase in accordance with embodiments of the present disclosure.

FIG. 4 shows an oxygen dilution scheme in accordance with embodiments of the present disclosure. In some aspects, the method of decreasing the oxygen content may comprise an oxygen dilution scheme. The oxygen dilution scheme dilutes the dispersed gas phase within the broth with nitrogen to reduce the oxygen concentration below the LOC of the dispersed gaseous phase. As shown in FIG. 4, nitrogen is fed to the bioreactor to dilute the oxygen in the dispersed gaseous phase before a separate gas phase mixture forms in the headspace and effluent gas. In some aspects, the nitrogen feed stream can be supplied to the bioreactor at an upper portion of the fermentation broth. The oxygen dilution scheme dilutes the dispersed gaseous phase in the fermentation broth prior to separation of the dispersed gas into the headspace and effluent gas with a suitable dilution gas stream, e.g., a gas stream depleted of oxygen, an inert gas stream, or a gas stream that has a high concentration of a flammable gas (e.g., pure hydrogen gas).

The oxygen dilution scheme comprises diluting the dispersed gaseous phase including the unreacted oxygen with a suitable dilution agent. In some aspects, the dilution agent can be a stream depleted of oxygen or an inert gas stream. In some aspects, the dilution agent may comprise nitrogen, hydrogen, carbon dioxide, or combinations thereof. In some aspects, the dilution agent can be a stream comprising less than 6.0 vol. % of oxygen, e.g., less than 5.9 vol. %, less than 5.5 vol. %, less than 5.0 vol. %, less than 4.0 vol. %, less than 3.0 vol. %, less than 2.0 vol. %, less than 1.0 vol. %, less than 0.5 vol. %, less than 0.1 vol. %, less than 0.01 vol. %, or alternatively, no oxygen. For example, the dilution agent may consist of an inert gas.

By decreasing the oxygen concentration to below the LOC for flammability, e.g., 6 vol. % for a hydrogen/air mixture, the method reduces the degree of flammability of the gas mixture and diminishes the risk of deflagration or explosions. In some aspects, the method of decreasing the oxygen content comprises diluting the dispersed gas phase with an inert gas, e.g., nitrogen, before a separate bulk gas phase forms in the headspace of the bioreactor. The method reduces the oxygen concentration within a safety margin below the LOC for flammability of the gas mixture.

In some aspects, the dilution agent is introduced to the bioreactor as a recycle stream to the bioreactor, e.g., a recycle stream comprising nitrogen or other gases from the fermentation process. In some aspects, the oxygen concentration is diluted by adding a hydrogen, nitrogen, carbon dioxide recycle stream at an upper portion of the fermentation broth. The unreacted hydrogen and carbon dioxide is recycled to an upper portion of the fermentation broth rather than at the bottom of the fermenter to achieve recycle as well as dilute the oxygen in the gaseous phase of the broth. The dilution agent is fed to the reactor to reduce the oxygen concentration below the LOC for flammability. Without the aforementioned oxygen destruction (e.g., removal) and dilution schemes, bioreactors would need to be built with thicker/stronger walls in order to safely contain the potentially flammable mixture, and such bioreactors would be more expensive.

In some aspects, the oxygen dilution scheme and the oxygen removal scheme can be used in combination to reduce the oxygen concentration.

EMBODIMENTS

Embodiment 1

A method for controlling oxygen concentration during aerobic biosynthesis, the method comprising: feeding an oxygen-containing gas into a bioreactor containing a microorganism, wherein a flammable gas fermentation feedstock component is within the bioreactor; reacting at least a portion of the oxygen from the oxygen-containing gas with the microorganism; forming a broth including a gaseous phase dispersed within the broth, the gaseous phase comprising unreacted oxygen from the oxygen-containing gas; reducing the concentration of the unreacted oxygen in the gaseous phase to less than the limiting oxygen concentration (LOC) for flammability of the flammable gas feedstock component, wherein the reducing comprises diluting the unreacted oxygen with a dilution agent; and separating the gaseous phase from the broth.

Embodiment 2

An embodiment of embodiment 1, wherein the dilution agent comprises a gas stream comprising one or more of nitrogen, carbon dioxide, and hydrogen.

Embodiment 3

An embodiment of embodiment 1 or 2, wherein the dilution agent comprises less than 5 vol. % oxygen.

Embodiment 4

An embodiment of any embodiment of embodiment 1-3, wherein the oxygen-containing gas comprises greater than 21 vol. % oxygen.

Embodiment 5

An embodiment of any embodiment of embodiment 1-4, wherein the oxygen-containing gas comprises air.

Embodiment 6

An embodiment of any embodiment of embodiment 1-5, wherein the gaseous phase separated from the broth comprises oxygen at a concentration less than 85% of the LOC.

Embodiment 7

An embodiment of any embodiment of embodiment 1-6, wherein the gaseous phase separated from the broth comprises less than 6 vol. % oxygen.

Embodiment 8

An embodiment of any embodiment of embodiment 1-7, wherein the step of reducing the concentration of the unreacted oxygen occurs prior to the step of separating the gaseous phase from the broth.

Embodiment 9

An embodiment of any embodiment of embodiment 1-8, wherein the microorganism comprises *C. necator* or *C. metallidurans*.

Embodiment 10

An embodiment of any embodiment of embodiment 1-9, wherein the bioreactor is selected from the group consisting of a single fermenter, multiple fermenters in series, a stirred-tank fermenter, a non-stirred tank fermenter, a membrane fermenter, a fixed-bed fermenter, a fluidized-bed fermenter, a single autoclave, multiple autoclaves in series, a plug flow fermenter, a pneumatically agitated fermenter, a gas-lift fermenter with an external loop having forced-circulation, a bubble-column fermenter, a fixed (packed) bed column fermenter, a horizontal single fermenter with multiple compartments, and multistage column fermenters.

Embodiment 11

An embodiment of any embodiment of embodiment 1-10, wherein the separating comprises separating the gaseous phase from the broth to a headspace of the bioreactor.

Embodiment 12

An embodiment of any embodiment of embodiment 1-11, further comprising feeding a flammable gas composition into the bioreactor.

Embodiment 13

An embodiment of embodiment 12, wherein the flammable gas composition comprises hydrogen.

Embodiment 14

An embodiment of embodiment 12 or 13, wherein the oxygen-containing gas and the flammable gas composition are continuously fed to the bioreactor in separate feeds.

Embodiment 15

A method for controlling oxygen concentration during aerobic biosynthesis, the method comprising: feeding an oxygen-containing gas into a bioreactor containing a microorganism, wherein a flammable gas fermentation feedstock component is within the bioreactor; reacting at least a portion of the oxygen from the oxygen-containing gas with the microorganism; forming a broth including a gaseous phase dispersed within the broth, the gaseous phase comprising unreacted oxygen from the oxygen-containing gas; reducing the concentration of the unreacted oxygen in the gaseous phase to less than the LOC for flammability of the flammable gas feedstock component, wherein the reducing comprises adsorbing or reacting the unreacted oxygen with a solid oxygen catalyst; and separating the gaseous phase from the broth.

Embodiment 16

An embodiment of embodiment 15, wherein oxygen-containing gas comprises greater than 21 vol. % oxygen.

Embodiment 17

An embodiment of embodiment 15 or 16, wherein the oxygen-containing gas comprises air.

Embodiment 18

An embodiment of any embodiment of embodiment 15-17, wherein the gaseous phase separated from the broth comprises oxygen at a concentration less than 85% of the LOC.

Embodiment 19

An embodiment of any embodiment of embodiment 15-18, wherein the gaseous phase separated from the broth comprises less than 6 vol. % oxygen.

Embodiment 20

An embodiment of any embodiment of embodiment 15-19, wherein the step of reducing the concentration of the unreacted oxygen occurs prior to the step of separating the gaseous phase from the broth.

Embodiment 21

An embodiment of any embodiment of embodiment 15-20, wherein the microorganism comprises *C. necator* or *C. metallidurans*.

Embodiment 22

An embodiment of any embodiment of embodiment 15-21, wherein the bioreactor is selected from the group consisting of a single fermenter, multiple fermenters in series, a stirred-tank fermenter, a non-stirred tank fermenter, a membrane fermenter, a fixed-bed fermenter, a fluidized-bed fermenter, a single autoclave, multiple autoclaves in series, a plug flow fermenter, a pneumatically agitated fermenter, a gas-lift fermenter with an external loop having forced-circulation, a bubble-column fermenter, a fixed (packed) bed column fermenter, a horizontal single fermenter with multiple compartments, and multistage column fermenters.

Embodiment 23

An embodiment of any embodiment of embodiment 15-22, wherein separating comprises separating the gaseous phase from the broth to a headspace of the bioreactor.

Embodiment 24

An embodiment of any embodiment of embodiment 15-23, further comprising feeding a flammable gas composition into the bioreactor.

Embodiment 25

An embodiment of embodiment 24, wherein the flammable gas composition comprises hydrogen.

Embodiment 26

An embodiment of embodiment 24 or 25, wherein the oxygen-containing gas and the flammable gas composition are continuously fed to the bioreactor in separate feeds.

Embodiment 27

A method for controlling oxygen concentration during aerobic biosynthesis, the method comprising: feeding an oxygen-containing gas into a bioreactor containing a microorganism, wherein a flammable gas fermentation feedstock component is within the bioreactor; reacting at least a portion of the oxygen from the oxygen-containing gas with the microorganism; forming a broth including a gaseous phase dispersed within the broth, the gaseous phase comprising unreacted oxygen from the oxygen-containing gas; reducing the concentration of the unreacted oxygen in the gaseous phase to less than the LOC for flammability of the flammable gas feedstock component, wherein the reducing comprises absorbing the unreacted oxygen in an oxygen absorbing liquid; and separating the gaseous phase from the broth.

Embodiment 28

An embodiment of embodiment 27, wherein oxygen-containing gas comprises greater than 21 vol. % oxygen.

Embodiment 29

An embodiment of embodiment 27 or 28, wherein the oxygen-containing gas comprises air.

Embodiment 30

An embodiment of any embodiment of embodiment 27-29, wherein the gaseous phase separated from the broth comprises oxygen at a concentration less than 85% of the LOC.

Embodiment 31

An embodiment of any embodiment of embodiment 27-30, wherein the gaseous phase separated from the broth comprises less than 6 vol. % oxygen.

Embodiment 32

An embodiment of any embodiment of embodiment 27-31, wherein the step of reducing the concentration of the unreacted oxygen occurs prior to the step of separating the gaseous phase from the broth.

Embodiment 33

An embodiment of any embodiment of embodiment 27-32, wherein the microorganism comprises *C. necator* or *C. metallidurans*.

Embodiment 34

An embodiment of any embodiment of embodiment 27-33, wherein the bioreactor is selected from the group consisting of a single fermenter, multiple fermenters in series, a stirred-tank fermenter, a non-stirred tank fermenter, a membrane fermenter, a fixed-bed fermenter, a fluidized-bed fermenter, a single autoclave, multiple autoclaves in series, a plug flow fermenter, a pneumatically agitated fermenter, a gas-lift fermenter with an external loop having forced-circulation, a bubble-column fermenter, a fixed (packed) bed column fermenter, a horizontal single fermenter with multiple compartments, and multistage column fermenters.

Embodiment 35

An embodiment of any embodiment of embodiment 27-34 wherein the separating comprises separating the gaseous phase from the broth to a headspace of the bioreactor.

Embodiment 36

An embodiment of any embodiment of embodiment 27-35, further comprising feeding a flammable gas composition into the bioreactor.

Embodiment 37

An embodiment of embodiment 36, wherein the flammable gas composition comprises hydrogen.

Embodiment 38

An embodiment of embodiment 36 or 37, wherein the oxygen-containing gas and the flammable gas composition are continuously fed to the bioreactor in separate feeds.

While the disclosure has been described in detail, modifications within the spirit and scope of the disclosure will be readily apparent to those of skill in the art. It should be understood that aspects of the disclosure and portions of various embodiments and various features recited above and/or in the appended claims may be combined or interchanged either in whole or in part. In the foregoing descriptions of the various embodiments, those embodiments which refer to another embodiment may be appropriately combined with other embodiments as will be appreciated by one of ordinary skill in the art. Furthermore, those of ordinary skill in the art will appreciate that the foregoing description is by way of example only, and is not intended to limit the disclosure. All U.S. patents and publications cited herein are incorporated by reference in their entirety. References recited herein are provided with full details as follows:

K. T. Klasson, M. D. Ackerson, E. C. Clausen and J. L. Gaddy, "Fermenter Design for Synthetic Gas Fermentations", Fuel (1991), 70, 605-614.

Ishizaki A, Tanaka K, Taga N (2001) Microbial production of poly-D-3-hydroxybutyrate from CO2. Appl Microbiol Biotechnol 57:6-12.

K. Tanaka 1994 Production of Poly-D-3-Hydroxybutyric acid from Carbon Dioxide by a Two Stage Culture Method Employing *Alcaligenes eutrophus* ATCC 17697.

Maddipati P1, Atiyeh H K, Bellmer D D, Huhnke R L. Ethanol production from syngas by *Clostridium* strain P11 using corn steep liquor as a nutrient replacement to yeast extract. Bioresoure Technol. 2011 June; 102(11): 6494-501.

Jugder B-E, Chen Z, Ping D T T, Lebhar H, Welch J, Marquis C P. An analysis of the changes in soluble hydrogenase and global gene expression in *Cupriavidus necator* (*Ralstonia eutropha*) H16 grown in heterotrophic diauxic batch culture. *Microbial Cell Factories*. 2015; 14:42. doi:10.1186/s12934-015-0226-4.

C J Brigham, C S Gai, J Lu, D R Speth, R M Worden, A J Sinskey. Engineering *Ralstonia eutropha* for Production of Isobutanol from CO2, H2 and O2. Advanced Biofuels and Bioproducts (2013) Chapter 39, Springer Science and Business, New York.

Phillips, J. R.; Huhnke, R. L.; Atiyeh, H. K. Syngas Fermentation: A Microbial Conversion Process of Gaseous Substrates to Various Products. Fermentation 2017, 3, 28.

G W Jones, R E Kenny. Prevention of Gas Explosions by Controlling Oxygen Concentration. Industrial and Engineering Chemistry 1935, 27, 1344-1346.

What is claimed is:

1. A method for controlling oxygen concentration during aerobic biosynthesis, the method comprising:
    feeding an oxygen-containing gas into a bioreactor containing a microorganism, wherein a flammable gas fermentation feedstock component is within the bioreactor, wherein the oxygen-containing gas and the flammable gas fermentation feedstock are continuously fed to the bioreactor in separate feeds;
    contacting at least a portion of the oxygen from the oxygen-containing gas with the microorganism to allow a maximum amount of oxygen to be consumed by the microorganism;
    forming a fermentation broth including a gaseous phase dispersed within the fermentation broth, the gaseous phase comprising unreacted oxygen from the oxygen-containing gas;
    reducing the concentration of the unreacted oxygen in the gaseous phase to less than the limiting oxygen concentration (LOC) for flammability of the flammable gas feedstock component, wherein the reducing comprises.
    diluting the unreacted oxygen with a dilution agent;
    adsorbing or reacting the unreacted oxygen with a solid oxygen catalyst, or
    absorbing the unreacted oxygen in an oxygen absorbing liquid, or a combination thereof, and
    separating the gaseous phase from the fermentation broth into a headspace of the bioreactor;
    wherein the step of reducing the concentration of unreacted oxygen in the gaseous phase is performed prior to the separation of gaseous phase from the fermentation broth and after the microorganism consumes the maximum amount of oxygen during the aerobic biosynthesis process.

2. method of claim 1, wherein the reducing comprises diluting the oxygen with a dilution agent.

3. The method of claim 1, wherein the dilution agent comprises a gas stream comprising one or more of nitrogen, carbon dioxide, and hydrogen.

4. The method of claim 1, wherein the dilution agent comprises less than 5 vol. % oxygen.

5. The method of claim 1, wherein the oxygen-containing gas comprises greater than 21 vol. % oxygen.

6. The method of claim 1, wherein the gaseous phase separated from the fermentation broth comprises less than 6 vol. % oxygen.

7. The method of claim 1, wherein the microorganism comprises *Cupriavidus necator* (*C. necator*) or *Cupriavidus metallidurans* (*C. metallidurans*).

8. The method of claim 1, further comprising feeding a flammable gas composition into the bioreactor, wherein the flammable gas composition comprises hydrogen.

9. The method of claim 1, wherein the reducing comprises adsorbing or reacting the unreacted oxygen with a solid oxygen catalyst.

10. The method of claim 9, wherein oxygen-containing gas comprises greater than 21 vol. % oxygen.

11. The method of claim 9, wherein the gaseous phase separated from the fermentation broth comprises less than 6 vol. % oxygen.

12. The method of claim 9, wherein the microorganism comprises *Cupriavidus necator* (*C. necator*) or *Cupriavidus metallidurans* (*C. metallidurans*).

13. The method of claim 9, further comprising feeding a flammable gas composition into the bioreactor, wherein the flammable gas composition comprises hydrogen.

14. The method of claim 1, wherein the reducing comprises absorbing the unreacted oxygen in an oxygen absorbing liquid.

15. The method of claim 14, wherein oxygen-containing gas comprises greater than 21 vol. % oxygen.

16. The method of claim 14, wherein the gaseous phase separated from the fermentation broth comprises less than 6 vol. % oxygen.

17. The method of claim 14, wherein the microorganism comprises *Cupriavidus necator* (*C. necator*) or *Cupriavidus metallidurans* (*C. metallidurans*).

18. The method of claim 14, further comprising feeding a flammable gas composition into the bioreactor, wherein the flammable gas composition comprises hydrogen.

* * * * *